US012697083B2

(12) United States Patent
Gong et al.

(10) Patent No.: US 12,697,083 B2
(45) Date of Patent: Aug. 4, 2026

(54) SYSTEMS AND METHODS FOR PLAQUE IDENTIFICATION, PLAQUE COMPOSITION ANALYSIS, AND PLAQUE STABILITY DETECTION

(71) Applicant: SHANGHAI UNITED IMAGING HEALTHCARE CO., LTD., Shanghai (CN)

(72) Inventors: Zhenhuan Gong, Shanghai (CN); Yufei Mao, Shanghai (CN); Xiong Yang, Shanghai (CN); Saisai Su, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 856 days.

(21) Appl. No.: 18/046,487

(22) Filed: Oct. 13, 2022

(65) Prior Publication Data

US 2023/0115927 A1 Apr. 13, 2023

(30) Foreign Application Priority Data

Oct. 13, 2021 (CN) .......................... 202111191473.0
Oct. 18, 2021 (CN) .......................... 202111210997.X
Dec. 23, 2021 (CN) .......................... 202111591583.6

(51) Int. Cl.
*A61B 6/00* (2024.01)
*A61B 6/50* (2024.01)
(Continued)

(52) U.S. Cl.
CPC ............ *A61B 6/5217* (2013.01); *A61B 6/504* (2013.01); *G06T 7/0012* (2013.01); *G06T 7/73* (2017.01);
(Continued)

(58) Field of Classification Search
CPC ......... A61B 6/5217; A61B 6/504; G06T 7/73; G06T 7/0012; G06T 2207/20084;
(Continued)

(56) References Cited

U.S. PATENT DOCUMENTS 4,945,478 A * 7/1990 Merickel ................ A61B 5/055
382/131
8,131,336 B2 3/2012 Liu et al.
(Continued)

FOREIGN PATENT DOCUMENTS

CN 104794708 A 7/2015
CN 105303571 A 2/2016
(Continued)

OTHER PUBLICATIONS

Liu et al. NPL "On Retinal Vessel Segmentation Using FCN". (Year: 2019).*
(Continued)

*Primary Examiner* — Andrew W Bee
*Assistant Examiner* — Winta Gebreslassie
(74) *Attorney, Agent, or Firm* — METIS IP LLC

(57) ABSTRACT

The embodiments of the present disclosure provides methods for processing a plaque implemented on at least one machine each of which has at least one processor and at least one storage device for. The method may include: obtaining a plurality of images corresponding to a target vessel; processing the plurality of images; and determining plaque information based on a processing result. The plaque information may include at least one of an identification result of a target plaque, plaque composition distribution, or a detection result of plaque stability.

20 Claims, 13 Drawing Sheets

(51) Int. Cl.

| | |
|---|---|
| *G06T 7/00* | (2017.01) |
| *G06T 7/73* | (2017.01) |
| *G06V 10/26* | (2022.01) |
| *G06V 10/44* | (2022.01) |
| *G06V 10/50* | (2022.01) |
| *G06V 10/774* | (2022.01) |
| *G06V 20/64* | (2022.01) |

(52) U.S. Cl.

CPC .............. *G06V 10/26* (2022.01); *G06V 10/44* (2022.01); *G06V 10/50* (2022.01); *G06V 10/774* (2022.01); *G06V 20/64* (2022.01); *G06T 2207/20084* (2013.01); *G06T 2207/30101* (2013.01); *G06T 2207/30172* (2013.01)

(58) Field of Classification Search

CPC ........... G06T 2207/30101; G06T 2207/30172; G06V 20/64; G06V 10/50; G06V 10/44; G06V 10/26; G06V 10/774

See application file for complete search history.

(56) References Cited

U.S. PATENT DOCUMENTS

| | | | |
|---|---|---|---|
| 10,762,637 | B2 | 9/2020 | Gulsun et al. |
| 2005/0043614 | A1* | 2/2005 | Huizenga ........... A61B 5/02007 600/427 |
| 2008/0009702 | A1* | 1/2008 | Liu .................... A61B 5/02007 600/410 |
| 2016/0235373 | A1 | 8/2016 | Sharma et al. |
| 2020/0410675 | A1 | 12/2020 | Wang et al. |
| 2021/0085397 | A1 | 3/2021 | Passerini et al. |
| 2023/0301722 | A1 | 9/2023 | Choi et al. |
| 2023/0326032 | A1* | 10/2023 | Li ........................... G06N 3/08 382/156 |

FOREIGN PATENT DOCUMENTS

| | | | |
|---|---|---|---|
| CN | 107730497 | A | 2/2018 |
| CN | 108542390 | A | 9/2018 |
| CN | 110490040 | A | 11/2019 |
| CN | 111062943 | A | 4/2020 |
| CN | 111145173 | A | 5/2020 |
| CN | 111583260 | A | 8/2020 |
| CN | 111598891 | A | 8/2020 |
| CN | 111681226 | A | 9/2020 |
| CN | 112085730 | A | 12/2020 |
| CN | 112288731 | A | 1/2021 |
| CN | 113192031 | A | 7/2021 |
| CN | 113298831 | A | 8/2021 |
| CN | 113393427 | A | 9/2021 |
| CN | 113763543 | A | 12/2021 |
| WO | 2019231844 | A1 | 12/2019 |
| WO | 2020087838 | A1 | 5/2020 |

OTHER PUBLICATIONS

Qian, Chunjun et al., An Integrated Method for Atherosclerotic Carotid Plaque Segmentation in Ultrasound Image, Computer Methods and Programs in Biomedicine, 153: 19-32, 2018.

Christos P. Loizou et al., An Integrated System for the Segmentation of Atherosclerotic Carotid Plaque Ultrasound Video, IEEE Transactions on Ultrasonics, Ferroelectrics, and Frequency Control, 61(1): 86-101, 2014.

Lakis Christodoulou et al., Full-Automated System for the Segmentation of the Common Carotid Artery in Ultrasound Images, IEEE 2012 5th International Symposium on Communications, Control and Signal Processing, 2012, 6 pages.

The Extended European Search Report in European Application No. 22201470.6 mailed on Mar. 9, 2023, 9 pages.

Shi, Feng et al., Intracranial Vessel Wall Segmentation Using Convolutional Neural Networks, IEEE Transactions on Biomedical Engineering, 66(10): 2840-2847, 2019.

Antonio Tejero-De-Pablos et al., Segmentation of Calcified and Non-Calcified Plaques on CCTA-CPR Scans via Masking of the Artery Wall, Arxiv.Org, 2022, 12 pages.

* cited by examiner

100

Figure 2:
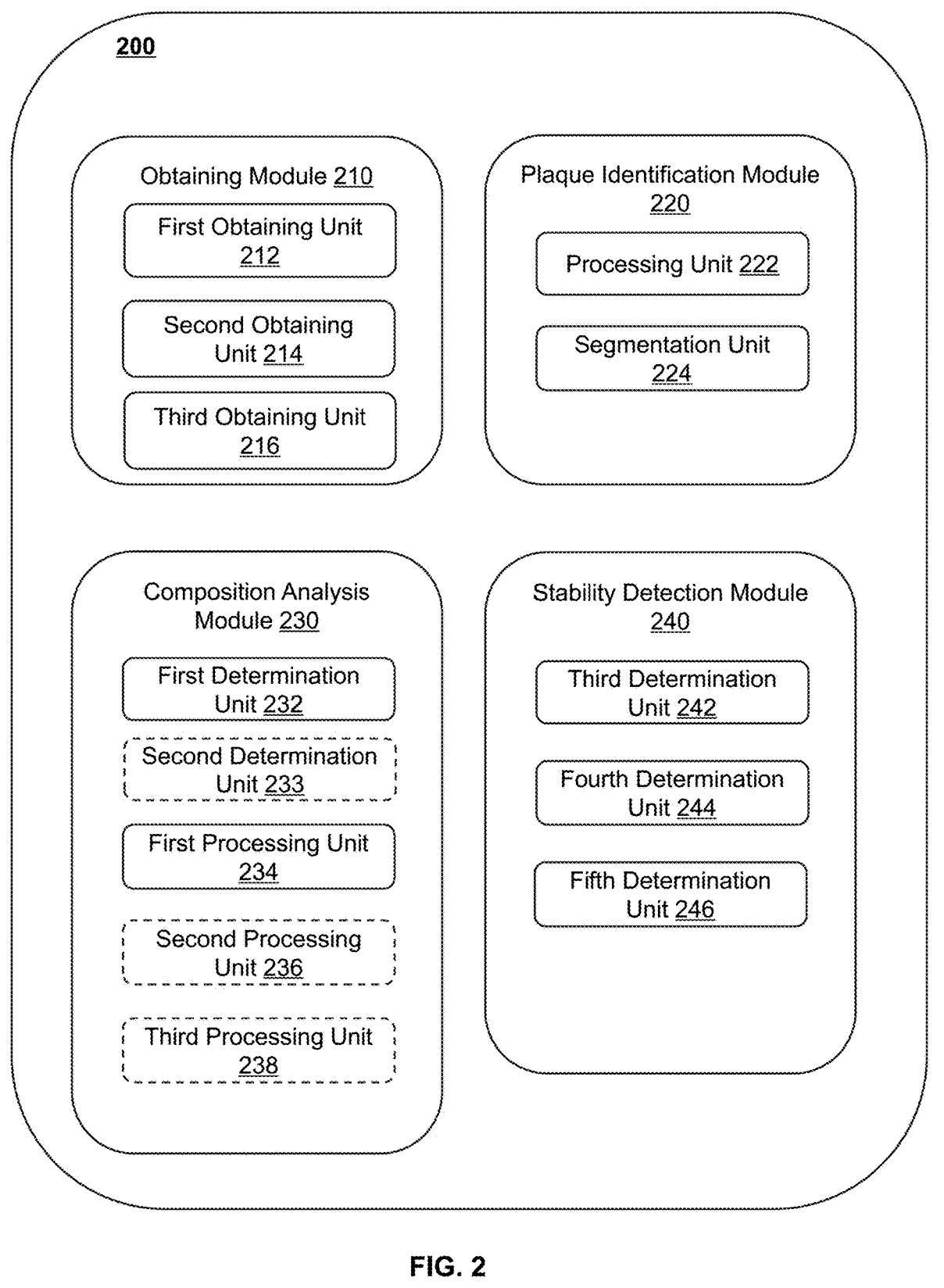

200

Obtaining Module 210

First Obtaining Unit
212

Second Obtaining
Unit 214

Third Obtaining Unit
216

Plaque Identification Module
220

Processing Unit 222

Segmentation Unit
224

Composition Analysis
Module 230

First Determination
Unit 232

Second Determination
Unit 233

First Processing Unit
234

Second Processing
Unit 236

Third Processing Unit
238

Stability Detection Module
240

Third Determination
Unit 242

Fourth Determination
Unit 244

Fifth Determination
Unit 246

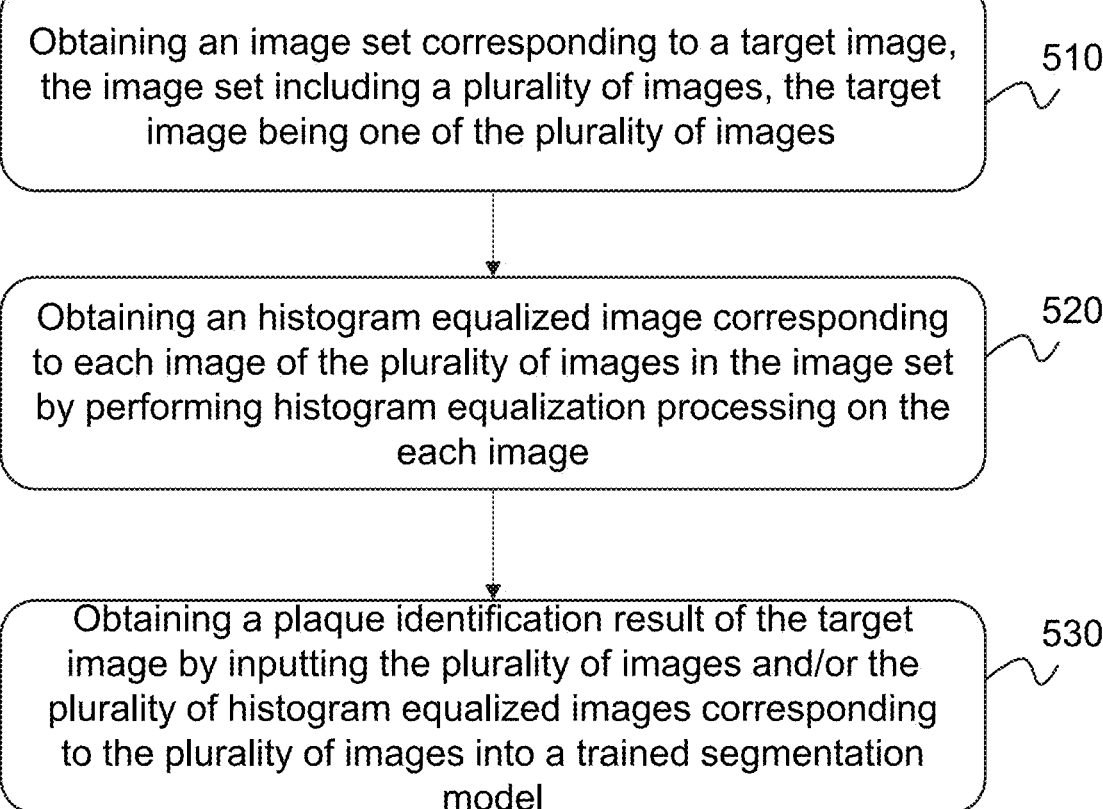

Obtaining an image set corresponding to a target image, the image set including a plurality of images, the target image being one of the plurality of images          510

Obtaining an histogram equalized image corresponding to each image of the plurality of images in the image set by performing histogram equalization processing on the each image          520

Obtaining a plaque identification result of the target image by inputting the plurality of images and/or the plurality of histogram equalized images corresponding to the plurality of images into a trained segmentation model          530

FIG. 5

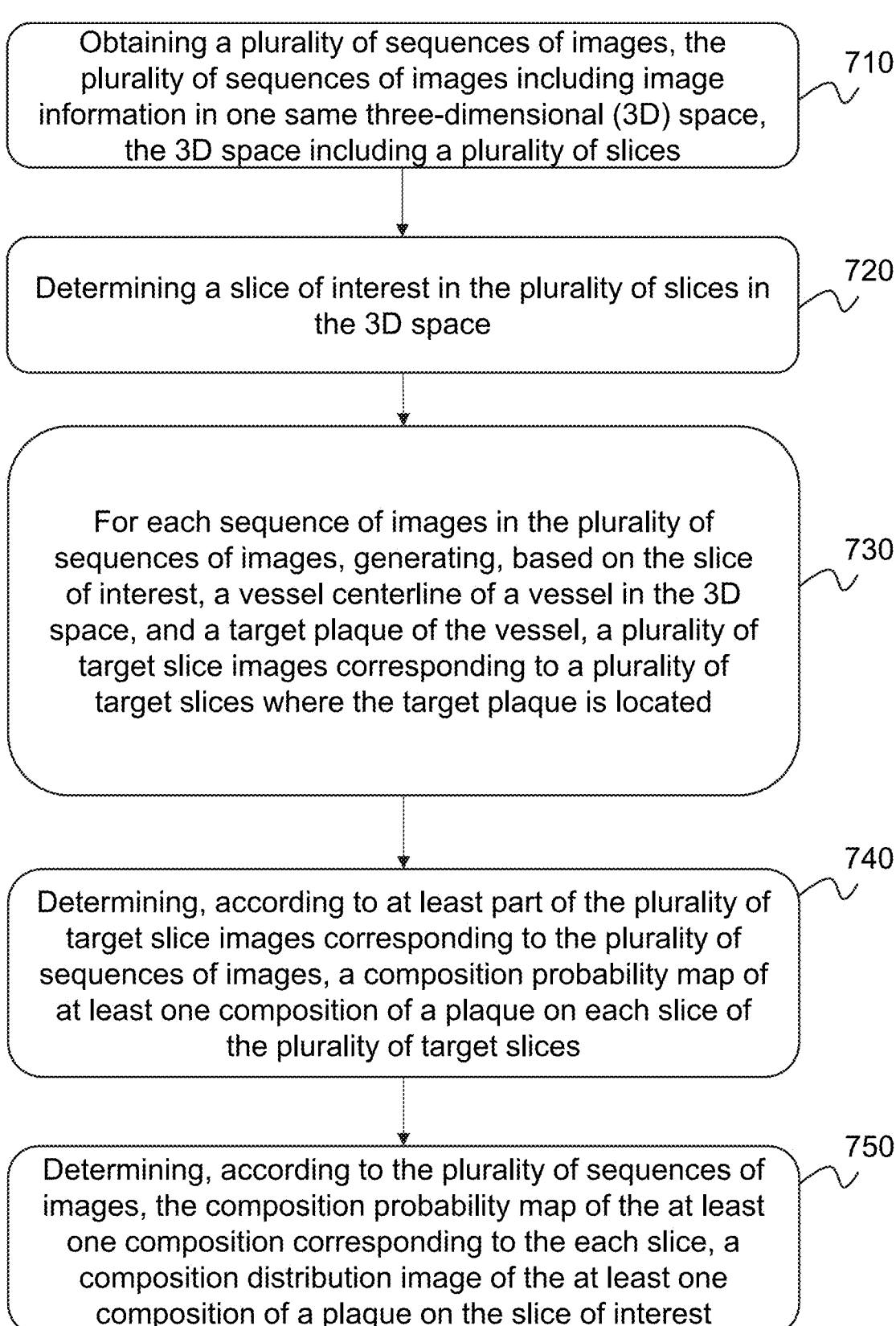

Obtaining a plurality of sequences of images, the plurality of sequences of images including image information in one same three-dimensional (3D) space, the 3D space including a plurality of slices
710

Determining a slice of interest in the plurality of slices in the 3D space
720

For each sequence of images in the plurality of sequences of images, generating, based on the slice of interest, a vessel centerline of a vessel in the 3D space, and a target plaque of the vessel, a plurality of target slice images corresponding to a plurality of target slices where the target plaque is located
730

Determining, according to at least part of the plurality of target slice images corresponding to the plurality of sequences of images, a composition probability map of at least one composition of a plaque on each slice of the plurality of target slices
740

Determining, according to the plurality of sequences of images, the composition probability map of the at least one composition corresponding to the each slice, a composition distribution image of the at least one composition of a plaque on the slice of interest
750

FIG. 7

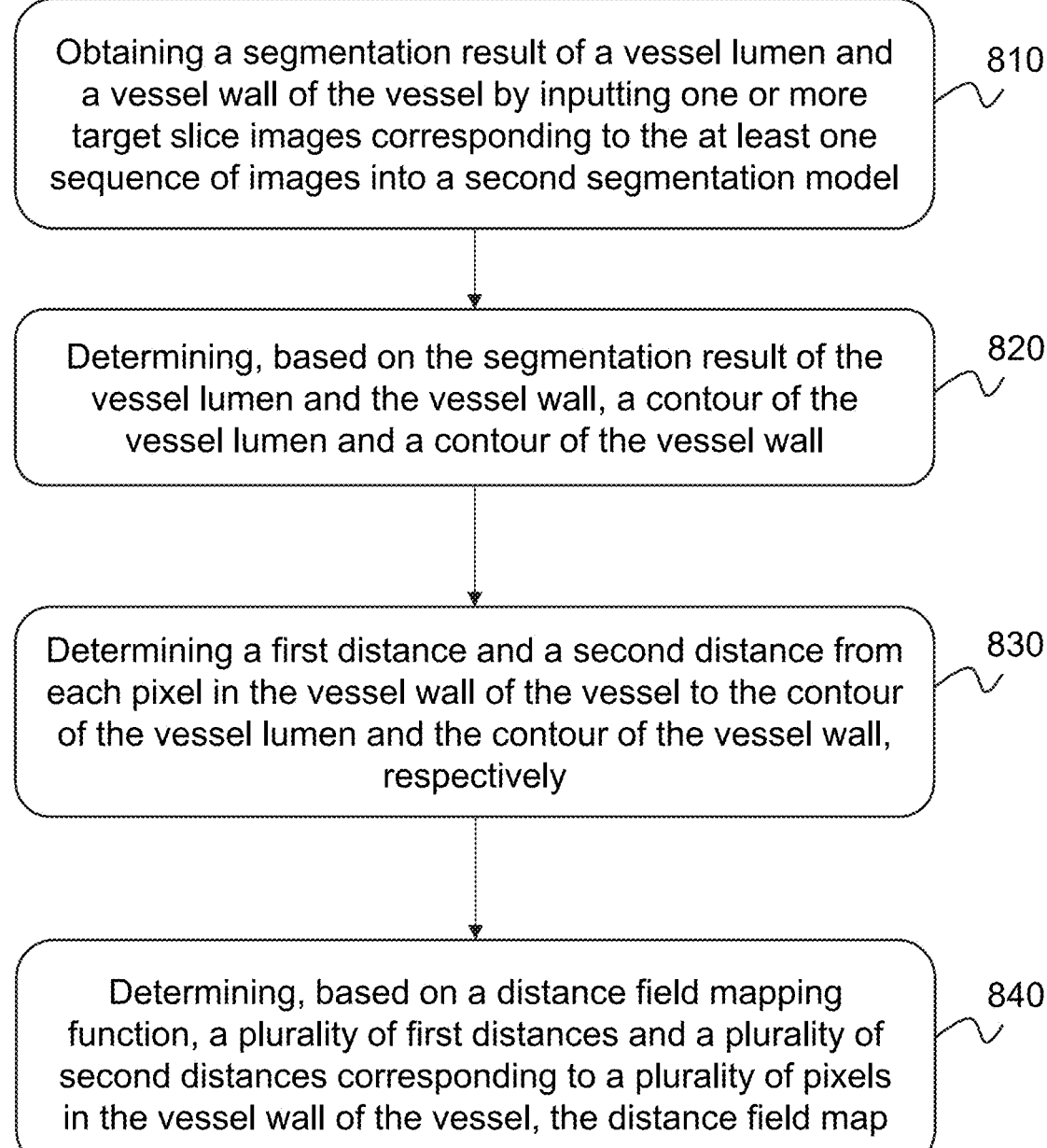

Obtaining a segmentation result of a vessel lumen and a vessel wall of the vessel by inputting one or more target slice images corresponding to the at least one sequence of images into a second segmentation model

810

Determining, based on the segmentation result of the vessel lumen and the vessel wall, a contour of the vessel lumen and a contour of the vessel wall

820

Determining a first distance and a second distance from each pixel in the vessel wall of the vessel to the contour of the vessel lumen and the contour of the vessel wall, respectively

830

Determining, based on a distance field mapping function, a plurality of first distances and a plurality of second distances corresponding to a plurality of pixels in the vessel wall of the vessel, the distance field map

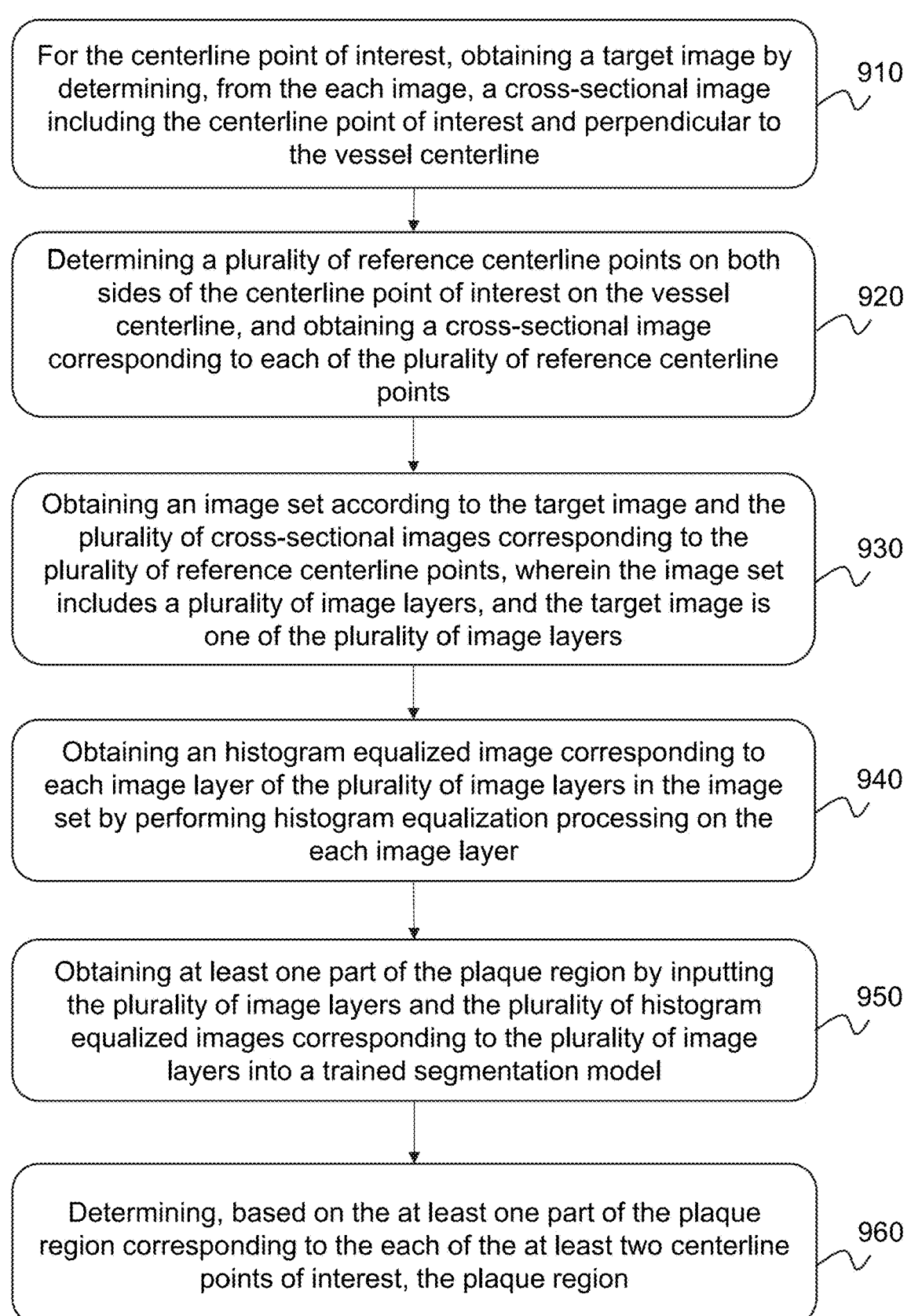

For the centerline point of interest, obtaining a target image by determining, from the each image, a cross-sectional image including the centerline point of interest and perpendicular to the vessel centerline
910

Determining a plurality of reference centerline points on both sides of the centerline point of interest on the vessel centerline, and obtaining a cross-sectional image corresponding to each of the plurality of reference centerline points
920

Obtaining an image set according to the target image and the plurality of cross-sectional images corresponding to the plurality of reference centerline points, wherein the image set includes a plurality of image layers, and the target image is one of the plurality of image layers
930

Obtaining an histogram equalized image corresponding to each image layer of the plurality of image layers in the image set by performing histogram equalization processing on the each image layer
940

Obtaining at least one part of the plaque region by inputting the plurality of image layers and the plurality of histogram equalized images corresponding to the plurality of image layers into a trained segmentation model
950

Determining, based on the at least one part of the plaque region corresponding to the each of the at least two centerline points of interest, the plaque region
960

FIG. 9 vessel Centerline

SYSTEMS AND METHODS FOR PLAQUE IDENTIFICATION, PLAQUE COMPOSITION ANALYSIS, AND PLAQUE STABILITY DETECTION

CROSS-REFERENCE TO RELATED APPLICATIONS

This application claims priority to Chinese Patent Application No. 202111191473.0, filed on Oct. 13, 2021, Chinese Patent Application No. 202111210997.X, filed on Oct. 18, 2021, and Chinese Patent Application No. 202111591583.6, filed on Dec. 23, 2021, the entire contents of each of which are hereby incorporated by reference.

TECHNICAL FIELD

The present disclosure generally relates to the technical field of image processing, and in particular, to systems and methods for plaque identification, plaque composition analysis, and plaque stability detection.

BACKGROUND

Morbidity and mortality of cardiovascular and cerebrovascular diseases are increasing year by year in the world. Cardiovascular and cerebrovascular diseases have gradually become diseases with the highest mortality. Studies have shown that nature of plaque plays an important role in occurrence, development, and prognosis of cardiovascular diseases. Processing and analysis of plaques is particularly important. Images with different contrasts may be provided to doctor(s) for observe. Generally, a pixel-to-pixel connection between images with different contrasts may need to be observed and determined by the doctor(s) with naked eyes, and pixel values of pixels corresponding to images with different contrasts may only be judged by the naked eyes. In analysis of plaque composition, a commonly used solution in clinical practice is to compare signal levels of a suspicious region and surrounding sternocleidomastoid muscles. Generally, the comparison may merely be conducted by subjective analysis using the naked eyes. In addition, the vulnerability of vessel plaque(s) may be basically judged by a doctor through reading images. However, manual processing and analysis may be cumbersome, inefficient, and unrepeatable, and heavily rely on the doctor's diagnosing experiences in reading images. Although few studies assist in judging plaque vulnerability based on automatic algorithms, most of which rely on a single data source, thereby making accuracy of plaque vulnerability judgment low.

Therefore, it is desirable to provide systems and methods for plaque identification, plaque composition analysis, and plaque stability detection to obtain quantification information (such as a size and/or a position of a plaque) with relatively high accuracy, thereby greatly improving work efficiency of doctors and reducing workload of doctors.

SUMMARY

In one aspect of the present disclosure, a method implemented on at least one machine each of which has at least one processor and at least one storage device for identifying a plaque is provided. The method may include obtaining an image set corresponding to a target image, the image set including a plurality of images, the target image being one of the plurality of images; obtaining a histogram equalized image corresponding to each image of the plurality of images in the image set by performing histogram equalization processing on the each image; and obtaining a plaque identification result of the target image by inputting the plurality of images and/or the plurality of histogram equalized images corresponding to the plurality of images into a trained segmentation model.

In another aspect of the present disclosure, a method implemented on at least one machine each of which has at least one processor and at least one storage device for analyzing plaque composition is provided. The system may include: obtaining a plurality of sequences of images, the plurality of sequences of images including image information in one same three-dimensional (3D) space, the 3D space includes a plurality of slices; determining a slice of interest in the plurality of slices in the 3D space; for each sequence of images in the plurality of sequences of images, generating, based on the slice of interest, a vessel centerline of a vessel in the 3D space, and a target plaque of the vessel, a plurality of target slice images corresponding to a plurality of target slices where the target plaque is located, wherein the plurality of target slices include the slice of interest, and the plurality of target slice images include a slice image corresponding to the slice of interest; determining, according to at least part of the plurality of target slice images corresponding to the plurality of sequences of images, a composition probability map of at least one composition of a plaque on each slice of the plurality of target slices; and determining, according to the plurality of sequences of images, the composition probability map of the at least one composition corresponding to the each slice, a composition distribution image of the at least one composition of a plaque on the slice of interest.

In still another aspect of the present disclosure, a method implemented on at least one machine each of which has at least one processor and at least one storage device for detecting plaque stability is provided. The system may include: obtaining a plurality of multi-modality images of a target vessel, wherein the plurality of multi-modality images includes a plurality of images generated by different imaging manners; determining a plaque region and a vessel region in each image of the plurality of images by segmenting the each image; determining, according to the plaque region and the vessel region of the each image, feature quantification information corresponding to the each image; and determining, according to the feature quantification information corresponding to the each image, a detection result of plaque stability of the target vessel.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 2 is a schematic diagram illustrating an exemplary plaque processing system according to some embodiments of the present disclosure;

FIG. 5 is a flowchart illustrating an exemplary process for identifying a plaque according to some embodiments of the present disclosure;

FIG. 7 is a flowchart illustrating an exemplary process for analyzing plaque composition according to some embodiments of the present disclosure;

FIG. 8 is a flowchart illustrating an exemplary process for determining a distance field map according to some embodiments of the present disclosure;

FIG. 9 is a flowchart illustrating an exemplary process for determining a target plaque according to some embodiments of the present disclosure;

DETAILED DESCRIPTION

Figure 1:
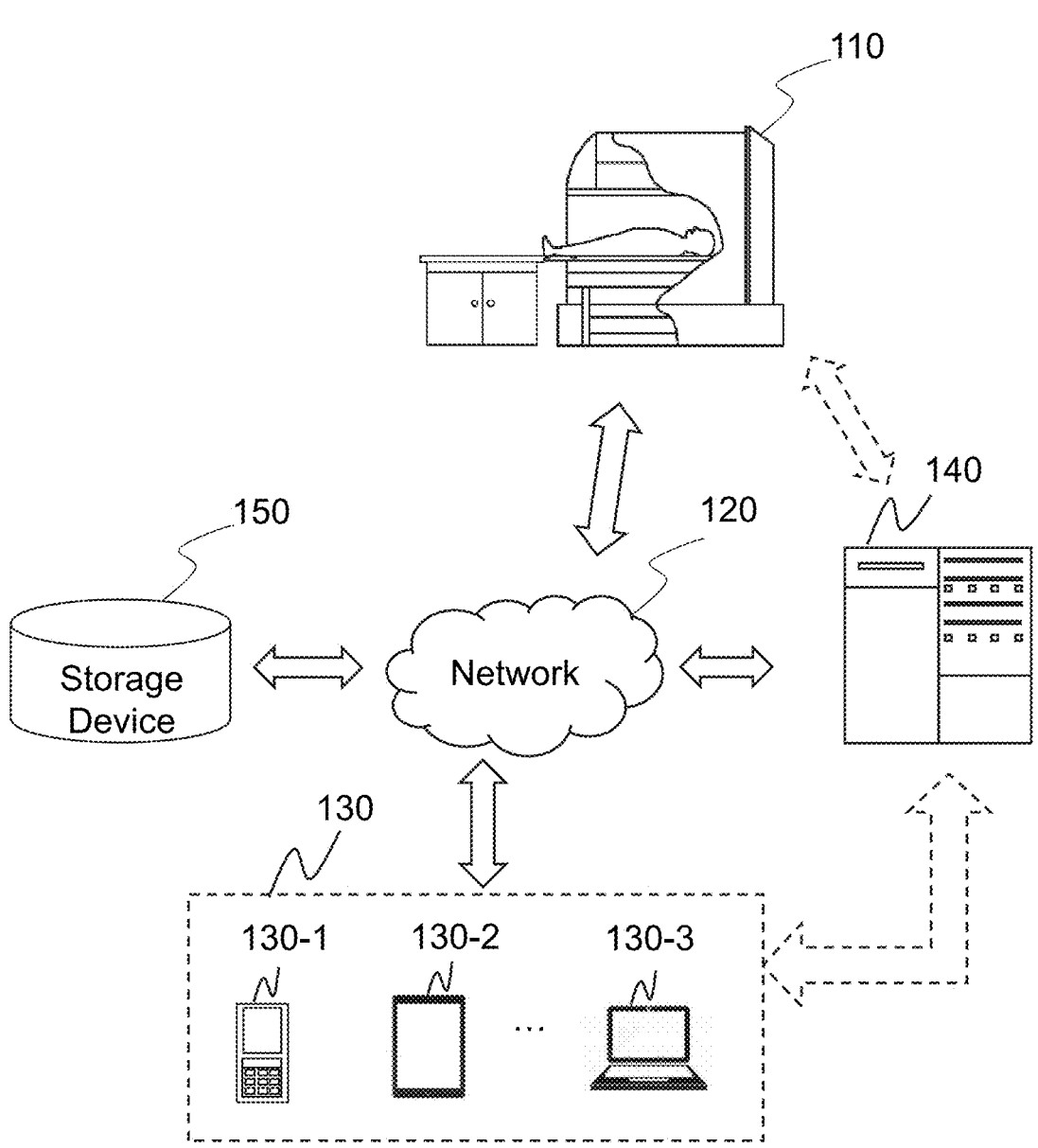
FIG. 1 is a schematic diagram illustrating an exemplary application scenario of a plaque processing system according to some embodiments of the present disclosure.

In order to more clearly illustrate the technical solutions related to the embodiments of the present disclosure, a brief introduction of the drawings referred to the description of the embodiments is provided below. Obviously, the drawings described below are only some examples or embodiments of the present disclosure. Those having ordinary skills in the art, without further creative efforts, may apply the present disclosure to other similar scenarios according to these drawings. Unless obviously obtained from the context or the context illustrates otherwise, the same numeral in the drawings refers to the same structure or operation.

It should be understood that the "system," "device," "unit," and/or "module" used herein are one method to distinguish different components, elements, parts, sections, or assemblies of different levels. However, if other words can achieve the same purpose, the words can be replaced by other expressions.

As used in the disclosure and the appended claims, the singular forms "a," "an," and "the" include plural referents unless the content clearly dictates otherwise; the plural forms may be intended to include singular forms as well. In general, the terms "comprise," "comprises," and/or "comprising," "include," "includes," and/or "including," merely prompt to include steps and elements that have been clearly identified, and these steps and elements do not constitute an exclusive listing. The methods or devices may also include other steps or elements.

The flowcharts used in the present disclosure illustrate operations that the system implements according to the embodiment of the present disclosure. It should be understood that the foregoing or following operations may not necessarily be performed exactly in order. Instead, the operations may be processed in reverse order or simultaneously. Besides, one or more other operations may be added to these processes, or one or more operations may be removed from these processes.

An existing plaque segmentation scheme may generally perform image recognition processing on a certain arterial image (such as a carotid artery) to determine whether there is a plaque in a carotid artery image and a position of the plaque. However, in the process of plaque segmentation, only information in a carotid plaque image may be obtained, resulting in an inaccurate segmentation result. In a composition analysis of a vessel plaque, after determining a suspicious region in an imaging sequence, a user may compare signal levels of the suspicious region and a surrounding sternocleidomastoid muscle region using naked eyes, and obtain a composition analysis result according to the signal levels observed with the naked eyes. The obtained composition analysis result may be not objective enough and may have low precision. In addition, a traditional method for detecting plaque stability may also have a problem of low detection accuracy.

In some embodiments of the present disclosure, intelligent methods for plaque processing are provided. Through intelligent processing, accuracy of plaque identification, plaque composition analysis, and plaque stability detection can be improved, thereby enhancing work efficiency.

FIG. 1 is a schematic diagram illustrating an exemplary application scenario of a plaque processing system according to some embodiments of the present disclosure. As shown in FIG. 1, the application scenario 100 may include a medical device 110, a network 120, a terminal 130, a processing device 140, and a storage device 150. The components in the application scenario 100 may be connected in various ways. Merely by way of example, as shown in FIG. 1, the medical device 110 may be connected to the processing device 140 via the network 120. For example, the medical device 110 may be directly connected to the processing device 140. As another example, the storage device 150 may be connected to the processing device 140 directly or via the network 120. As yet another example, the terminal 130 may be directly connected to the processing device 140 or connected to the processing device 140 via the network 120.

The medical device 110 may be a device configured to obtain medical image(s). For example, the medical device 110 may obtain one or more vessel cross-sectional images, and vessel plaque images of a human body or an animal. The medical device 110 may include a medical ultrasound device, a medical scanning device, etc.

In some embodiments, the medical device 110 may include a single-modality scanning device and/or a multi-modality scanning device. The single-modality scanning device may include a computed tomography (CT) device, a positron emission computed tomography (PET) scanning device, a magnetic resonance imaging (MRI) device, an X-ray scanning device, etc. The multi-modality scanning device may include an X-ray imaging-magnetic resonance imaging (X-ray-MRI) device, a positron emission computed tomography-X-ray imaging (PET-X-ray) device, a single photon emission computed tomography-magnetic resonance imaging (SPECT-MRI) device, a positron emission computed tomography-computed tomography (PET-CT) scanning device, etc. The scanning devices are merely provided for the purpose of illustration, and are not intentioned to limit the scope of the present disclosure. As used herein, the terms of "imaging modality" or "modality" may refer to an imaging method or technique that collects, generates, processes, and/or analyzes imaging information of a target object.

The network 120 may include any suitable network that can facilitate the exchange of information and/or data for the application scenario 100. In some embodiments, one or more components of the application scenario 100 (e.g., the medical device 110, the terminal 130, the processing device 140, or the storage device 150) may communicate information and/or data with one or more other components of the application scenario 100 via the network 120. For example, the processing device 140 may obtain a medical image of a scanned object from the medical device 110 via the network 120. In some embodiments, the network 120 may include a wired network, a wireless network, or any combination thereof. In some embodiments, the network may be various topological structures such as a point-to-point topological structure, a shared topological structure, a centralized topological structure, or the like, or any combination thereof. In some embodiments, the network 120 may include one or more network access points. For example, the network 120 may include wired or wireless network access points.

The terminal 130 may include a mobile device 130-1, a tablet computer 130-2, a laptop computer 130-3, or the like, or any combination thereof. In some embodiments, the terminal 130 may interact with other compositions in the application scenario 100 via the network 120. For example, the terminal 130 may send one or more control instructions to the medical device 110 to obtain a medical image (e.g., a carotid artery image) of a scanning region of a human body. As another example, the terminal 130 may receive data such as a medical image sent by the medical device 110, etc. In some embodiments, the terminal 130 may receive information and/or instructions input by a user (such as, a user of the medical device 110, such as a doctor), and send the received information and/or instructions to the medical device 110 or the processing device 140 via the network 120. For example, the doctor may input an operation instruction to the medical device 110 through the terminal 130. In some embodiments, the terminal 130 may be part of the processing device 140. For example, the terminal 130 may be integrated with the processing device 140 as a control device for the medical device 110. In some embodiments, the terminal 130 may be omitted.

The processing device 140 may process data and/or information obtained from the medical device 110, the terminal 130 and/or the storage device 150. For example, the processing device 140 may obtain a medical image or a video of the human body. As another example, the processing device 140 may acquire, based on the medical device 110, a cross-sectional image of a vessel centerline, a vessel wall mask image, a plaque image of the human body. In some embodiments, the processing device 140 may acquire a medical image based on the medical device 110. For another example, the processing device 140 may process the medical image acquired by the medical device 110 to perform type identification, cost analysis, stability detection, etc., on a plaque in the medical image.

In some embodiments, the processing device 140 may be a single server or a server group. The server group may be centralized or distributed. In some embodiments, the processing device 140 may be local or remote. For example, the processing device 140 may assess information and/or data stored in or obtained by the medical device 110, the terminal 130 and/or the storage device 150 via the network 120. As another example, the processing device 140 may be directly connected to the medical device 110, the terminal 130, and/or the storage device 150 to access the stored or obtained information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 300. The computing device 300 may have one or more components shown in FIG. 3 in the present disclosure. More descriptions regarding the computing device 300 may be found in FIG. 3.

The storage device 150 may store data and/or instructions. In some embodiments, the storage device 150 may store data obtained from the medical device 110, the terminal 130 and/or the processing device 140. For example, the storage device 150 may store motion information of a target object preset by a user (e.g., a doctor, an imaging technician). In some embodiments, the storage device 150 may store data and/or instructions that the processing device 140 may execute or use to perform exemplary methods described in the present disclosure. For example, the storage device 150 may store instructions for the processing device 140 to perform the methods illustrated in the flowcharts. In some embodiments, the storage device 150 may include a mass storage, a removable storage, a volatile read-and-write memory, a read-only memory (ROM), or the like, or any combination thereof. In some embodiments, the storage device 150 may be implemented on the cloud platform.

In some embodiments, the storage device 150 may be connected to the network 120 to communicate with one or more components of the application scenario 100 (e.g., the medical device 110, the terminal 130, the processing device 140, etc.). One or more components of the application scenario 100 may access the data or instructions stored in the storage device 150 via the network 120. In some embodiments, the storage device 150 may be directly connected to or communicate with one or more components of the application scenario 100 (e.g., the medical device 110, the terminal 130, the processing device 140, etc.). In some embodiments, the storage device 150 may be part of the processing device 140.

It should be noted that the application scenario 100 is merely provided for the purpose of illustration, and is not intended to limit the scope of the present disclosure. For persons having ordinary skills in the art, a plurality of variations and modifications may be made under the teachings of the present disclosure. For example, the application scenario may further include a display device. As another example, each component of the application scenario 100 may have their own storage devices, or share a storage device. However, those variations and modifications do not depart from the scope of the present disclosure.

FIG. 2 is a schematic diagram illustrating an exemplary plaque processing system according to some embodiments of the present disclosure. As shown in FIG. 2, the plaque processing system 200 may include an obtaining module 210, a plaque identification module 220, a composition analysis module 230, and a stability detection module 240.

The obtaining module 210 may be configured to obtain a plurality of images relating to a plaque. In some embodiments, the obtaining module 310 may further include a first obtaining unit 212, a second obtaining unit 214, and a third obtaining unit 216.

In some embodiments, the first obtaining unit 212 may be configured to obtain image(s) relating to plaque identification. The images relating to plaque identification may be an image set (e.g., a cross-sectional image set) corresponding to a target image (e.g., a target cross-sectional image image).

The image set may include a plurality of images (e.g., cross-sectional images). The target image may be one of the plurality of images.

In some embodiments, the first obtaining unit 212 may be configured to: obtain a centerline point on a vessel centerline; designate, from a three-dimensional (3D) image, a cross-sectional image including the centerline point and perpendicular to the vessel centerline as the target image; determine a plurality of reference centerline points on both sides of the centerline point on the vessel centerline, obtain a cross-sectional image corresponding to each of the reference centerline points; and designate the target image and the cross-sectional image corresponding to each of the reference centerline points as the cross-sectional image set corresponding to the target cross-sectional image.

In some embodiments, the first obtaining unit 212 may be configured to take the centerline point as a starting point, and determine the plurality of reference centerline points on both sides of the centerline point on the vessel centerline based on a preset step size.

In some embodiments, the second obtaining unit 214 may be configured to obtain image(s) relating to plaque composition analysis. The images relating to plaque composition analysis may be a plurality of sequences of images of the target vessel. The plurality of sequences of images may include image information in a same 3D space. More descriptions may be found in FIG. 7 and the descriptions thereof.

In some embodiments, the third obtaining unit 216 may be configured to obtain image(s) relating to plaque stability detection. The images relating to plaque stability detection may be a plurality of multi-modality images of a target vessel. The plurality of vessel multi-modality images may include a plurality of vessel images generated by different imaging manners. More descriptions may be found in FIG. 12 and the descriptions thereof.

In some embodiments, the third obtaining unit 216 may be configured to obtain sample feature quantification information of a plurality of samples, and a plurality of vulnerability probability value labels corresponding to the sample feature quantification information of the plurality of samples.

The plaque identification module 220 may be configured to process the images relating to plaque identification and obtain a plaque identification result. In some embodiments, the plaque identification module 220 may further include a processing unit 222 and a segmentation unit 224.

The processing unit 222 may be configured to obtain a histogram equalized image corresponding to each image of the plurality of images by performing histogram equalization processing on the each image in the image set respectively.

The segmentation unit 224 may be configured to obtain a plaque identification result of the target image by inputting the plurality of images and the plurality of histogram equalized images corresponding to the plurality of images into a trained segmentation model.

In some embodiments, the segmentation unit 224 may also be configured to: obtain a vessel wall mask image (e.g., an image labelled by identifying and processing a vessel wall in the target image), and obtain the plaque identification result of the target image by inputting the vessel wall mask image, the plurality of images, and the plurality of histogram equalized images corresponding to the plurality of images into the trained segmentation model.

In some embodiments, the trained segmentation model may include a first plaque segmentation model. The segmentation unit 224 may be configured to: perform image normalization processing on the plurality of images and the plurality of histogram equalized images corresponding to the plurality of images; obtain first multi-channel input data by merging the vessel wall mask image, the plurality of normalized images, and the plurality of normalized histogram equalized images corresponding to the plurality of images; and obtain a first plaque identification result of the target image by inputting the first multi-channel input data into the first plaque segmentation model.

In some embodiments, the trained segmentation model may further include a plaque identification model and a second plaque segmentation model. The segmentation unit 224 may be further configured to: perform image normalization processing on the plurality of images, obtain second multi-channel input data by merging the vessel wall mask image and the plurality of normalized images; obtain a plaque type of a plaque in the target image by inputting the second multi-channel input data into the plaque identification model; in response to a determination that the plaque type of the plaque in the target image is a preset type, obtain a second plaque identification result of the target image by inputting the second multi-channel input data into the second plaque segmentation model; and obtain the plaque identification result of the target image according to the first plaque identification result and the second plaque identification result.

In some embodiments, the segmentation unit 224 may be further configured to: obtain the plaque identification result of the target image by taking a union set of the first plaque recognition result and the second plaque identification result.

The composition analysis module 230 may be configured to process images relating to plaque composition analysis, and determine a plaque composition analysis result. In some embodiments, the composition analysis module 230 may further include a first determination unit 232 and a first processing unit 234.

The first determination unit 232 may be configured to determine, according to at least a part of a plurality of target (vessel) slice images, a composition probability map of at least one composition of a plaque on each slice of a plurality of target slices.

The first processing unit 234 may be configured to determine, according to the plurality of sequences of images and the composition probability map of the at least one composition corresponding to the each slice, a composition distribution image of the at least one composition of a plaque on a slice of interest.

A device for composition analysis is provided in the embodiments of the present disclosure. For any target image in the plurality of sequences of images, N vessel cross-sectional images on N slices may be generated according to the vessel centerline and a target vessel plaque of the target image, wherein N is an integer greater than 0. According to the target vessel slice images on an $i^{th}$ slice, the composition probability map of the target vessel plaque on the $i^{th}$ slice may be determined. According to the composition probability map and the target vessel slice images on the $i^{th}$ slice, a composition distribution image corresponding to the target vessel plaque on the $i^{th}$ slice may be obtained. Based on the device for composition analysis provided in the embodiments of the present disclosure, the composition probability map of the target vessel plaque may be obtained by analysis, and then the composition probability map may be automatically and objectively analyzed to obtain the composition distribution image of the target vessel plaque, which can avoid influence of subjectivity in composition analysis through human eyes, so that the composition analysis result can be more objective and accurate, thereby improving accuracy and efficiency of composition analysis.

In some embodiments, the first processing unit 234 may be further configured to: obtain, according to the composition probability map and the vessel slice images on the $i^{th}$ slice, a composition distribution image corresponding to the target vessel plaque on the $i^{th}$ slice. The vessel slice image may include at least one of the target vessel slice image or a histogram equalized image obtained by performing histogram equalization processing on the target vessel slice image.

In some embodiments, the first processing unit 234 may be configured to: obtain, according to each target image and/or the target vessel slice images on the $i^{th}$ slice, an associated analysis image corresponding to the target vessel plaque; and obtain, according to the composition probability map, the vessel slice images on the $i^{th}$ slice, and the associated analysis image, the composition distribution image corresponding to the target vessel plaque on the $i^{th}$ slice. The associated analysis image may include at least one of a distance field map corresponding to the target vessel slice image, or an intensity relative map corresponding to each target vessel slice image.

In some embodiments, the first determination unit 232 may be further configured to obtain a region of interest (ROI) image corresponding to a plurality of imaging sequences by performing segmentation processing according to a plurality of sequences of images; obtain, according to the ROI image and a corresponding region of the ROI image in each target image, a statistical image corresponding to each target image; obtain, for any target image, according to the target vessel slice image on the $i^{th}$ slice and the statistical image corresponding to the target vessel, the intensity relative map, wherein the intensity relative map is configured to characterize a signal intensity relative result between the target vessel slice image and the statistical image; and obtain, according to the intensity relative map corresponding to each target image and composition distribution prior information, the composition probability map of the target vessel plaque on the $i^{th}$ slice.

In some embodiments, the composition analysis module 230 may further include a second processing unit 236, a second determination unit 233, and a third processing unit 238.

The second processing unit 236 may be configured to obtain a segmentation result of a vessel lumen and a vessel wall on the $i^{th}$ slice of plurality of sequences of images according to the target vessel slice image on the $i^{th}$ slice.

The second determination unit 233 may be configured to determine a first distance and a second distance from each pixel in the vessel wall to a contour of the vessel lumen and a contour of the vessel wall in the segmentation result of the vessel lumen and the vessel wall.

The third processing unit 238 may be configured to obtain a distance field map on the $i^{th}$ slice according to the first distance and the second distance corresponding to each pixel, wherein a pixel value of any pixel in the distance field image (also referred to as a distance field map) may be configured to characterize distances from the pixel to the contour of the vessel lumen and the contour of the vessel wall.

In some embodiments, the composition analysis module 230 may also include a fourth processing unit (not shown) configured to obtain the composition analysis result of the target vessel plaque by performing statistical analysis according to the composition distribution image on the Nth slice.

In some embodiments, the composition analysis module 230 may further include a first training unit. The first training unit may be configured to obtain a composition analysis network by training an analysis network according to a preset first training set. The first training set may include a plurality of first sample groups. The first sample group may include a plurality of sequences of sample images, sample vessel slice images corresponding to the plurality of sequences of sample images, and labelled composition distribution images of each slice of sample vessel slice images.

In some embodiments, the composition analysis module 230 may further include a second training unit. The second training unit may be configured to obtain a segmentation network by training an initial segmentation network according to a preset second training set. The second training set may include a plurality of second sample groups. The second sample group may include a plurality of sequences of sample images and labelled ROI images corresponding to the plurality of sequences of sample images.

The stability detection module 240 may be configured to detect plaque stability based on multi-modality data. In some embodiments, the stability detection module 240 may further include a third determination unit 242, a fourth determination unit 244, and a fifth determination unit 246.

The third determination unit 242 may be configured to determine a plaque region and a vessel region in each vessel image by performing feature detection on each vessel image of the vessel multi-modality images.

The fourth determination unit 244 may be configured to determine, according to the plaque region and the vessel region of each vessel image, feature quantification information corresponding to each vessel image. The feature quantification information may include quantification information of a plurality of plaque features corresponding to each vessel image, and quantification information of a plurality of vessel features corresponding to each vessel blood image. In some embodiments, the fourth determination unit 244 may be configured to, for each vessel image, determine plaque features according to the plaque region, and determine vessel features according to the vessel region; and obtain the feature quantification information by performing data quantification on the plaque features and the vessel features.

The fifth determination unit 246 may be configured to determine, according to the feature quantification information corresponding to one or more of the vessel images, a detection result of plaque stability of a target vessel. In some embodiments, the fifth determination unit 246 may also be configured to determine a vulnerability probability value of the plaque of the target vessel by inputting feature quantification information corresponding to one or more of the vessel images into a probability determination model; and determine the detection result of plaque stability based on the vulnerability probability value. In some embodiments, the probability determination model may be obtained by training an initial probability determination model using sample feature quantification information and a plurality of vulnerability probability value labels corresponding to the sample feature quantification information. In some embodiments, the probability determination model may include a regression model or a convolutional neural network model.

In some embodiments, the third determination unit 242 may also include a first plaque region determination unit and a second plaque region determination unit. The first plaque region determination unit may be configured determine the plaque region of the each vessel image by inputting the each vessel image into a plaque detection model. The plaque region detection model may be obtained by training a fully convolutional neural network model using a plurality of sample images and a plurality of plaque region labels corresponding to the plurality of sample images. A plurality of sample image may correspond to a plaque region label. The second plaque region determination unit may be configured to determine the plaque region and the vessel region according to the plaque region and the vessel image.

In some embodiments, the second plaque region determination unit may be further configured to determine, according to the plaque region and vessel image, an image to be processed; and determine a segmented plaque region and a segmented vessel region by inputting the image to be processed into a segmentation model. In some embodiments, the image to be processed may include at least one part of the plaque region and at least one part of the vessel region. The segmentation model may be obtained by training the convolutional neural network model using a plurality of sample images to be processed, a plurality of sample plaque labels corresponding to the plurality of sample images to be processed, and a plurality of sample vessel labels corresponding to the plurality of sample images to be processed.

In some embodiments, the stability detection module 240 may further include a model determination unit configured to obtain a regression model by calculating a coefficient in the regression model according to the sample feature quantification information of the plurality of samples and the plurality of vulnerability probability value labels corresponding to the sample feature quantification information of the plurality of samples.

It should be noted that the above description of the plaque processing system 200 and the components thereof is merely provided for the purpose of illustration, and is not intended to limit the scope of the embodiments of the present disclosure. For persons having ordinary skills in the art, modules may be combined in various ways or connected with other modules as sub-systems under the teaching of the present disclosure. For example, two or more components may share a storage device. Each component may also have its own storage device. Such modifications are all within the protection scope of the present disclosure.

Figure 3:
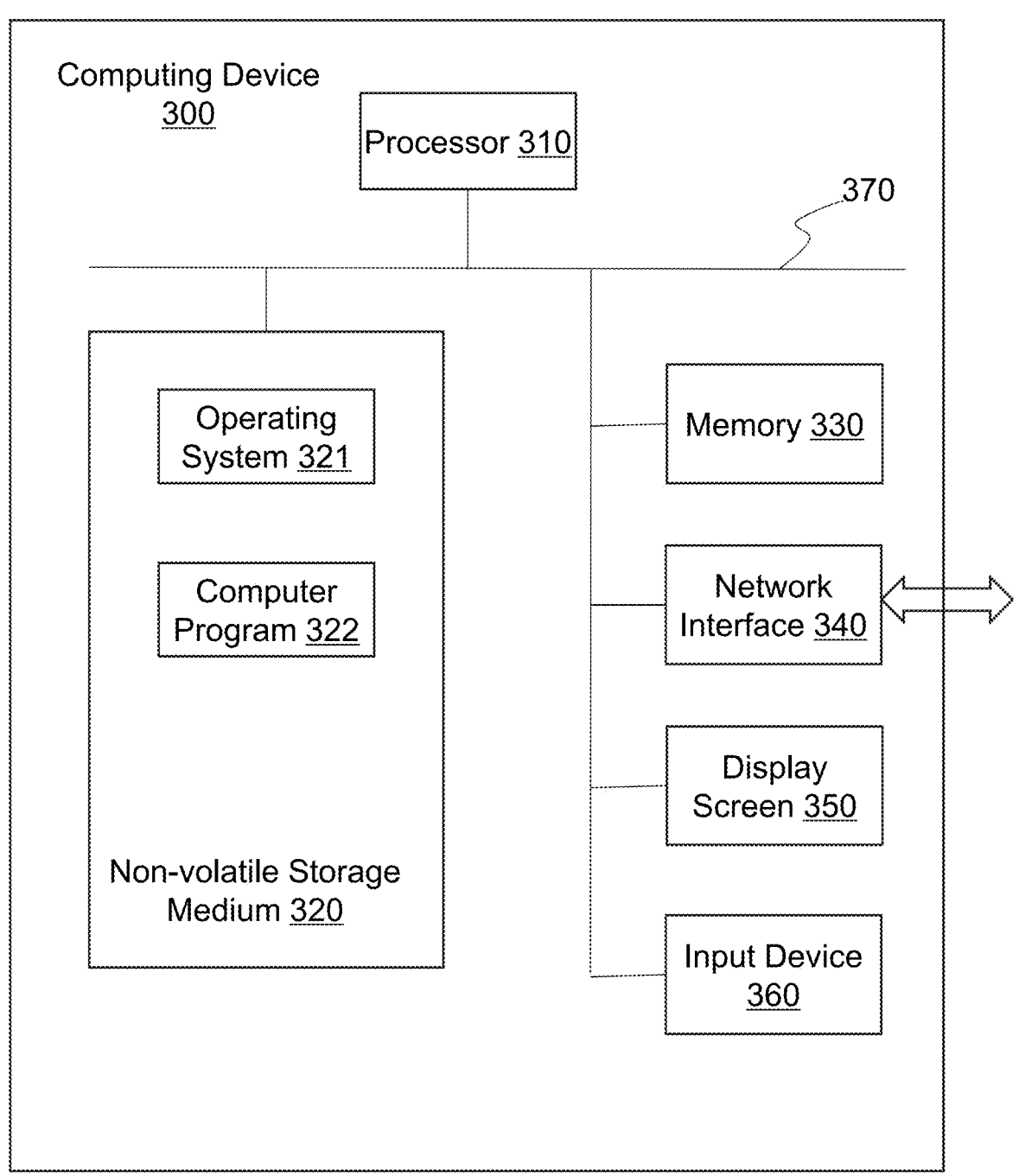
FIG. 3 is a schematic diagram of an exemplary computing device according to some embodiments of the present disclosure.

FIG. 3 is a schematic diagram of an exemplary computing device according to some embodiments of the present disclosure. The computing device 300 may be a server, as shown in FIG. 3, the computing device 300 may include a processor 310, a non-volatile storage medium 320, a memory 330, a network interface 340, a display screen 350, an input device 360, and a system bus 370.

The processor 310 may be configured to provide computing and control capabilities. In some embodiments, the processor 310 may execute computer instructions (e.g., program code) to perform the functions of the processing device 140 according to the methods described herein. The computer instructions may include a routine, a program, an object, a component, a signal, a data structure, a process, a module, a particular function described herein, etc. For example, the processor 310 may obtain images acquired by the medical device 110 from the storage device 150 and/or the terminal 130. In some embodiments, the processor 310 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device, any circuit or processor capable of executing one or more functions, or the like, or any combinations thereof.

The non-volatile storage medium 320 may be a computer-readable storage medium including, but is not limited to, a portable computer disk, a hard disk, a random access memory (RAM), a read-only memory (ROM), an erasable programmable read-only memory (EPROM or a flash memory), a portable compact disk read-only memory (CD-ROM), an optical storage device, a magnetic storage device, or any combination thereof. In some embodiments, the non-volatile storage medium 320 may store an operating system 321 and/or a computer program 322. The operating system 321 may include an operating system such as Windows, Linux, Mac OS, etc. The computer program 322 may be a computer application, program code, etc., executed by the processor 310. For example, the computer program 322 may include a variety of algorithms (e.g., a histogram equalization algorithm).

The memory 330 may store data and/or instructions. For example, the memory 330 may store the computer program 322 so that in some embodiments, the memory 330 may provide an environment for the operating system 321 and the computer program 322 in the non-volatile storage medium 320 to execute. In some embodiments, the memory 330 may also be configured to store a vessel image, a segmentation model (e.g., a first segmentation model, a second segmentation model, a third segmentation model, a fourth segmentation model), a probability determination model, etc.

The network interface 340 may be configured to be connected with an external terminal via the network. In some embodiments, the network interface 340 may be connected to a network (e.g., the network 120) to facilitate data communication. The network interface 340 may establish a connection between the processing device 140 an the medical device 110, the terminal 130, or the storage device 150. The connection may be a wired connection, a wireless connection, or any combination thereof, which may enable data transmission and reception. In some embodiments, the network interface 340 may be a standardized communication port, such as RS232, RS485, etc. In some embodiments, the network interface 340 may be a specially designed communication port. For example, the network interface 340 may be designed in accordance with the digital imaging and communications in medicine (DICOM) protocol.

The display screen 350 may be a device configured to present data or feedback data. The display screen 350 may be a display screen, etc. In some embodiments, the display screen 350 may be configured to present a medical image, a signal, a plaque processing result, etc. For example, the display screen 350 may feedback the plaque processing result (e.g., a plaque identification result, a plaque composition analysis result, and a plaque stability detection result) to a user.

The input device 360 may be configured to input a signal, data or information. In some embodiments, the input device 360 may enable a user to interact with the processor 310. In some embodiments, the input device 360 may include an input device. For example, the input device 250 may include a keyboard, a mouse, a touch screen, a microphone, a trackball, or the like, or a combination thereof.

The system bus 370 may be configured to connect various components of the computing device 300. For example, the system bus 370 may connect the processor 310, non-volatile storage medium 320, the memory 330, the network interface 340, the display screen 350, and the input device 360. In some embodiments, the system bus 370 may transmit data information, address information, control information, etc. to realize information exchange among various components of the computing device 300. For example, the processor 310 may send a control instruction to the memory 330 through the system bus 370 to obtain an image for processing, and send the processed information (e.g., the plaque identification result, the plaque composition analysis result, and the plaque stability detection result) to the display screen 350.

In some embodiments, when the computing device 300 is executed by the processor 310, a method for identifying a plaque, a method for analyzing plaque composition, and/or a method for detecting plaque stability may be implemented.

Those skilled in the art can understand that the structure shown in FIG. 3 is merely a block diagram of a part of the structure related to the solution of the present disclosure, and is not intended to limit the computing device to which the solution of the present disclosure is applied. A particular computing device may include more or fewer components than those shown in the figures, or combine certain components, or have different arrangements of components.

Figure 4:
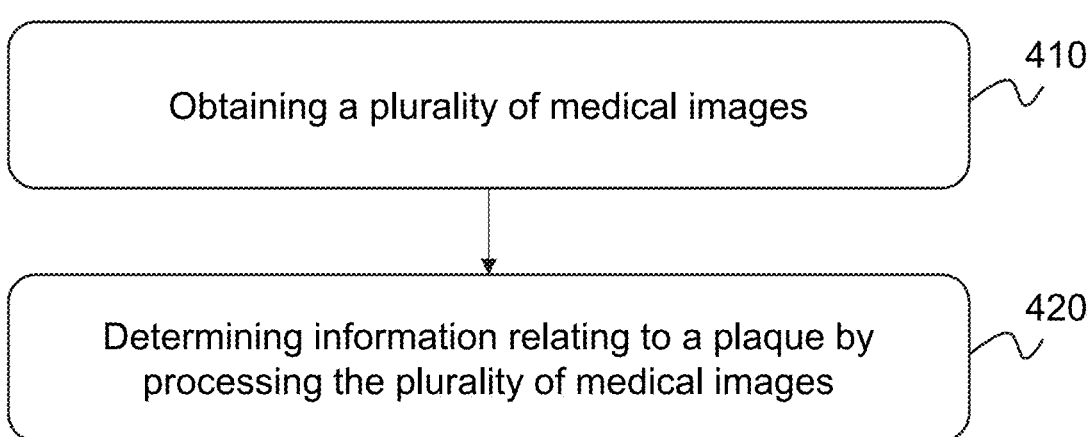
FIG. 4 is a flowchart illustrating an exemplary process for processing a plaque according to some embodiments of the present disclosure.

FIG. 4 is a flowchart illustrating an exemplary process for processing a plaque according to some embodiments of the present disclosure. In some embodiments, the process for processing a plaque may be performed by the processing device 140, the plaque processing system 200, or the computing device 300. For example, the process 400 may be stored in a storage device (e.g., the storage device 150) in a form of a program or an instruction. When the processing device 140 executes the program or the instruction, the process 400 may be implemented. The schematic diagram of operations of the process 400 presented below is intended to be illustrative. In some embodiments, the process may be accomplished with one or more additional operations not described and/or without one or more of the operations herein discussed. Additionally, the order in which the operations of the process 400 illustrated in FIG. 4 and described below is not intended to be limiting.

In 410, a plurality of images may be obtained. One or more of the plurality of images may include one or more plaques.

The plurality of images may include one or more medical images of an object (e.g., a human body, an animal) acquired by a medical device. The medical device may be a medical device 110 (e.g., a CT scanning device, a PET scanning device, an MRI scanning device), etc. The medical image may include an image of a certain part or region of the human body (e.g., a sternocleidomastoid region, a cervical artery region, etc.). The medical image may include a vessel and/or vessel cross-sectional image, a vessel wall mask image, a vessel plaque image, etc. In some embodiments, plaque identification, plaque composition analysis, and plaque stability detection, etc., may be performed on a plaque in the medical image. More descriptions may be found in FIG. 2.

In some embodiments, the medical image may also include a preliminarily analyzed and/or processed image (e.g., a histogram equalized image, a segmented image, an intensity relative map, etc.) associated with an image acquired by the medical device. The medical images may include a single image or a plurality of images (e.g., an image set, an imaging sequence). The medical image may be either a two-dimensional (2D) image or 3D image.

In some embodiments, the medical image may be obtained by the obtaining module 210 for subsequent processing (e.g., plaque identification, plaque composition analysis, plaque stability detection, etc.). In some embodiments, the medical image(s) may be preprocessed image(s). For example, the medical images may be a plurality of sequences of images spatially aligned that have been subjected to a registration operation.

In 420, information relating to a plaque may be determined by processing the plurality of images.

In some embodiments, the plurality of images may be processed one by one. For example, the processing device 140 may process grayscale change and/or color distortion, etc., of a single image, and/or may extract features (e.g., a vessel feature, a plaque feature) in a single image for analysis. In some embodiments, processing, comparison, matching analysis, etc., of two or more of the plurality of images may be performed. For example, histogram equalization processing, registration processing, etc., may be performed on the plurality of images.

In some embodiments, the images may be processed and/or analyzed through a trained segmentation model. For example, the plurality of images may be analyzed through a trained plaque segmentation model, a plaque identification model, a probability determination model, etc.

In some embodiments, the processing device 140 may determine information such as a plaque type of a plaque (e.g., a normal plaque, a calcified plaque), a plaque identification result, etc., based on the plaque image processing. More descriptions may be found in FIGS. 5-6 and descriptions thereof.

In some embodiments, the processing device 140 may determine, based on the plaque image processing, relevant information such as composition (e.g., calcification, hemorrhage, lipid necrosis nucleus) probability distribution, statistical information (e.g., a distribution position, a maximum area, a volume, a volume ratio, etc.) of each composition, etc., in the plaque image. More descriptions may be found in FIG. 7 and descriptions thereof.

In some embodiments, the processing device 140 may determine, based on the plaque image processing, the vulnerability probability value of the plaque, and then determine the stability of the plaque. More descriptions may be found in FIG. 12 and descriptions thereof.

FIG. 5 is a flowchart illustrating an exemplary process for identifying a plaque according to some embodiments of the present disclosure. In some embodiments, the process for identifying a plaque may be performed by the processing device 140, the plaque processing system 200, or the computing device 300. For example, the process 500 may be stored in a storage device (e.g., the storage device 150) in a form of a program or an instruction. When the processing device 140 executes the program or the instruction, the process 500 may be implemented. The schematic diagram of operations of the process 500 presented below is intended to be illustrative. In some embodiments, the process may be accomplished with one or more additional operations not described and/or without one or more of the operations herein discussed. In some embodiments, the process 500 may be performed by the plaque identification module 220. Additionally, the order in which the operations of the process 500 illustrated in FIG. 5 and described below is not intended to be limiting.

In 510, an image set corresponding to a target image may be obtained. The image set may include a plurality of images. The target image may be one of the plurality of images, or the target image may belong to the plurality of images.

The target image may refer to a target cross-sectional image. The target cross-sectional image may be one of a plurality of cross-sectional images. In some embodiments, a cross-sectional image set corresponding to the target cross-sectional image may be obtained. The cross-sectional image set may include the plurality of cross-sectional images.

In some embodiments, the plurality of images may be generated based on a same imaging sequence. In some embodiments, the images may include multi-contrast magnetic resonance images. In some embodiments, the plurality of images may include or be a plurality of images generated based on different imaging sequences for a same target object through a plurality of imaging technologies such as a T1-weighted imaging T1WI, a T2-weighted imaging T2WI, a TOF (time of light, based on a time-of-flight principle) imaging, an enhanced T1WI, etc.

In some embodiments, the plaque identification module 220 may obtain a vessel centerline in an initial 3D image, and obtain a centerline point of interest on the vessel centerline. The plaque identification module 220 may designate, from the initial 3D image, a cross-sectional image including the centerline point of interest and perpendicular to the vessel centerline as the target image. Furthermore, a plurality of reference centerline points on both sides of the centerline point of interest on the vessel centerline may be determined, and a cross-sectional image corresponding to each of the reference centerline points may be obtained. The target image and the plurality of cross-sectional images corresponding to the plurality of reference centerline points may be designated as the plurality of images of the image set corresponding to the target image.

In some embodiments, the plaque identification module 220 may obtain a 3D stereoscopic image. The 3D stereoscopic image may be a 3D carotid artery image, a 3D coronary artery image, etc. The 3D carotid artery image may be taken as an example for illustration as follows.

In some embodiments, for the obtained 3D carotid artery image, the plaque identification module 220 may extract a plurality of cross-sectional images along the vessel centerline, sort the images according to positions in the 3D carotid artery image, and extract sequentially arranged partial cross-sectional images from the plurality of cross-sectional images to form a cross-sectional image set. Each cross-sectional image set may include a target cross-sectional image. The target cross-sectional image may be any image in the cross-sectional image set, or may be a cross-sectional image in a middle position in the cross-sectional image set.

In some embodiments, a point on the vessel centerline may include a centerline point of interest of the vessel centerline. The centerline point of interest may be one or more vessel centerline points set by the user or the system.

In some embodiments, for the obtained 3D carotid artery image, the plaque identification module 220 may obtain the vessel centerline in the 3D initial image, obtain one or more centerline points of interest along the vessel centerline, for each centerline point of interest, designate, from the 3D carotid artery image, a cross-sectional image including the centerline point of interest and perpendicular to the vessel centerline as the target cross-sectional image, determine a plurality of reference centerline points on both sides (e.g., in a front-rear direction) of the centerline point of interest on the vessel centerline, and obtain a cross-sectional image corresponding to each of the reference centerline points from the 3D carotid artery image, and designate the target cross-sectional image and the plurality of cross-sectional images corresponding to the plurality of reference centerline points as the plurality of images of the cross-sectional image set corresponding to the target cross-sectional image.

In some embodiments, the plaques identification module 220 may take the centerline point of interest as a starting point, and determine the plurality of reference centerline points on both sides of the centerline point of interest on the vessel centerline based on a preset step size.

For example, at a centerline point of interest P, n reference centerline points on both sides of the point P on the vessel centerline may be respectively determined based on the preset step size (e.g., A), to obtain 2n reference centerline points.

In some embodiments, for the point P and the above 2n reference centerline points (i.e., totally (2n+1) points), the plaque identification module 220 (e.g., the processing unit 222) may reconstruct (2n+1) cross-sectional images with the (2n+1) points as centers and the XY axis of the centerline point of interest P as a direction to form a cross-sectional image set corresponding to the target cross-sectional image corresponding to the centerline point of interest P.

In 520, a histogram equalized image corresponding to each image of the plurality of images in the image set may be obtained by performing histogram equalization processing on the each image.

In some embodiments, the processing unit 222 may obtain a histogram equalized image corresponding to each cross-sectional image by performing histogram equalization processing on each cross-sectional image in the cross-sectional image set.

In some embodiments, for each cross-sectional image in the cross-sectional image set, the processing unit 222 may map grayscale values of the cross-sectional image using a histogram equalization algorithm to obtain the histogram equalized image corresponding to the each cross-sectional image.

In 530, a plaque identification result of the target image may be obtained by inputting the plurality of images and/or the plurality of histogram equalized images corresponding to the plurality of images into a trained segmentation model.

In some embodiments, the trained segmentation model may include a first plaque segmentation model. The segmentation unit 224 may obtain a vessel wall mask image corresponding to the target image and obtain a first plaque identification result of the target image by inputting the vessel wall mask image, the plurality of images, and the plurality of histogram equalized images corresponding to the plurality of images into the first plaque segmentation model.

The first plaque segmentation model may refer to a model configured to preliminarily identify a plaque. The first plaque identification result may refer to a plaque identification result of the target image output by the first plaque segmentation model. In some embodiments, the first plaque identification result may be an identification result obtained by identifying a plaque of a normal plaque type.

In some embodiments, the segmentation unit 224 may obtain a first plaque identification result of the target cross-sectional image by inputting the plurality of cross-sectional images and the histogram equalized image corresponding to each cross-sectional image into the trained plaque segmentation model. In some embodiments, the segmentation unit 224 may sequentially input the plurality of cross-sectional images and the histogram equalized image corresponding to each cross-sectional image into the trained first plaque segmentation model. In some embodiments, the segmentation unit 224 may put each cross-sectional image and the histogram equalized image corresponding to the each cross-sectional image together, and input each cross-sectional image and the histogram equalized image corresponding to each cross-sectional image together into the first plaque segmentation model.

In some embodiments, for a target training cross-sectional image, the segmentation unit 224 may perform plaque segmentation on the target training cross-sectional image using a single-channel model, and designate the segmented image as a gold standard G. Then, a multi-channel segmentation model may be obtained by training, based on a segmentation network and a segmentation loss, using a training cross-sectional image set corresponding to the target training cross-sectional image and the gold standard G. In some embodiments, the trained plaque segmentation model may be a multi-channel segmentation model.

In some embodiments, before inputting the plurality of cross-sectional images and the histogram equalized image corresponding to each cross-sectional image into the plaque segmentation model, the segmentation unit 224 may perform image normalization processing on each cross-sectional image and the histogram equalized image corresponding to each cross-sectional image, and then input the normalized images into the first plaque segmentation model.

In some embodiments of the present disclosure, the histogram equalized image may have one or more plaque boundaries that can be strengthened, and the plurality of cross-sectional images may increase an amount of plaque information obtained by the plaque segmentation model, and thus, the recognition accuracy of the first plaque segmentation model may be increased.

In some embodiments, the segmentation unit 224 may obtain the vessel wall mask image by identifying a vessel wall in the target image. The vessel wall mask image may be referred to as a vessel wall labelled map. The segmentation unit 224 may obtain a plaque identification result of the target cross-sectional image by inputting the vessel wall labelled map, the plurality of cross-sectional images, and the histogram equalized image corresponding to each cross-sectional image into the first plaque segmentation model.

The vessel wall labelled map may refer to an image obtained by labelling a contour of the vessel wall in the target image. The labelling of the contour of the vessel wall may refer to displaying the contour of the vessel wall in the target image using lines, so that the plaque segmentation model may accurately identify a position of the vessel wall. The plaque may be in an inner side of the vessel wall, so that a possible position of the plaque may be quickly located, thereby reducing unnecessary operations and improving efficiency. In some embodiments, the vessel wall labelled map may be obtained by performing a Gaussian model processing on the vessel wall in the target cross-sectional image.

In some embodiments, after the processing unit 222 performs image normalization processing on the plurality of images and the plurality of histogram equalized images corresponding to the plurality of images, the segmentation unit 224 may obtain first multi-channel input data by merging the vessel wall mask image, the plurality of normalized images, and the plurality of normalized histogram equalized images corresponding to the plurality of images, and obtain the first plaque identification result of the target image by inputting the first multi-channel input data into the first plaque segmentation model.

In some embodiments, a process of merging the vessel wall mask image, the plurality of cross-sectional images, and the histogram equalized image corresponding to each cross-sectional image may be to put each cross-sectional image and the histogram equalized image corresponding to the each cross-sectional image together, and then sort each cross-sectional image and the histogram equalized image corresponding to the each cross-sectional image according to an order of the multiple cross-sectional images. The vessel wall mask image may be put together with the target cross-sectional image and the histogram equalized image corresponding to the target cross-sectional image. Alternatively, a process of merging the vessel wall mask image, the plurality of cross-sectional images, and the histogram equalized image corresponding to each cross-sectional image may be to arrange the vessel wall mask image, the plurality of cross-sectional images, and the plurality of histogram equalized images in order. The segmentation unit 224 may obtain first multi-channel input data by performing the merging processing on the vessel wall mask image, the plurality of normalized images, and the plurality of normalized histogram equalized images corresponding to the plurality of images.

In some embodiments of the present disclosure, through multi-slice sections reconstruction, multi-slice vessel cross-sectional images may be reconstructed along the vessel direction at a position of the centerline point as a multi-channel input, and 3D information may be introduced while lightness of a 2D segmentation network is maintained, which can improve a network field of view and improve robustness of the segmentation result. In addition, the processing of histogram equalization can improve the contrast of the plaque, thereby improving the segmentation accuracy.

Figure 6:
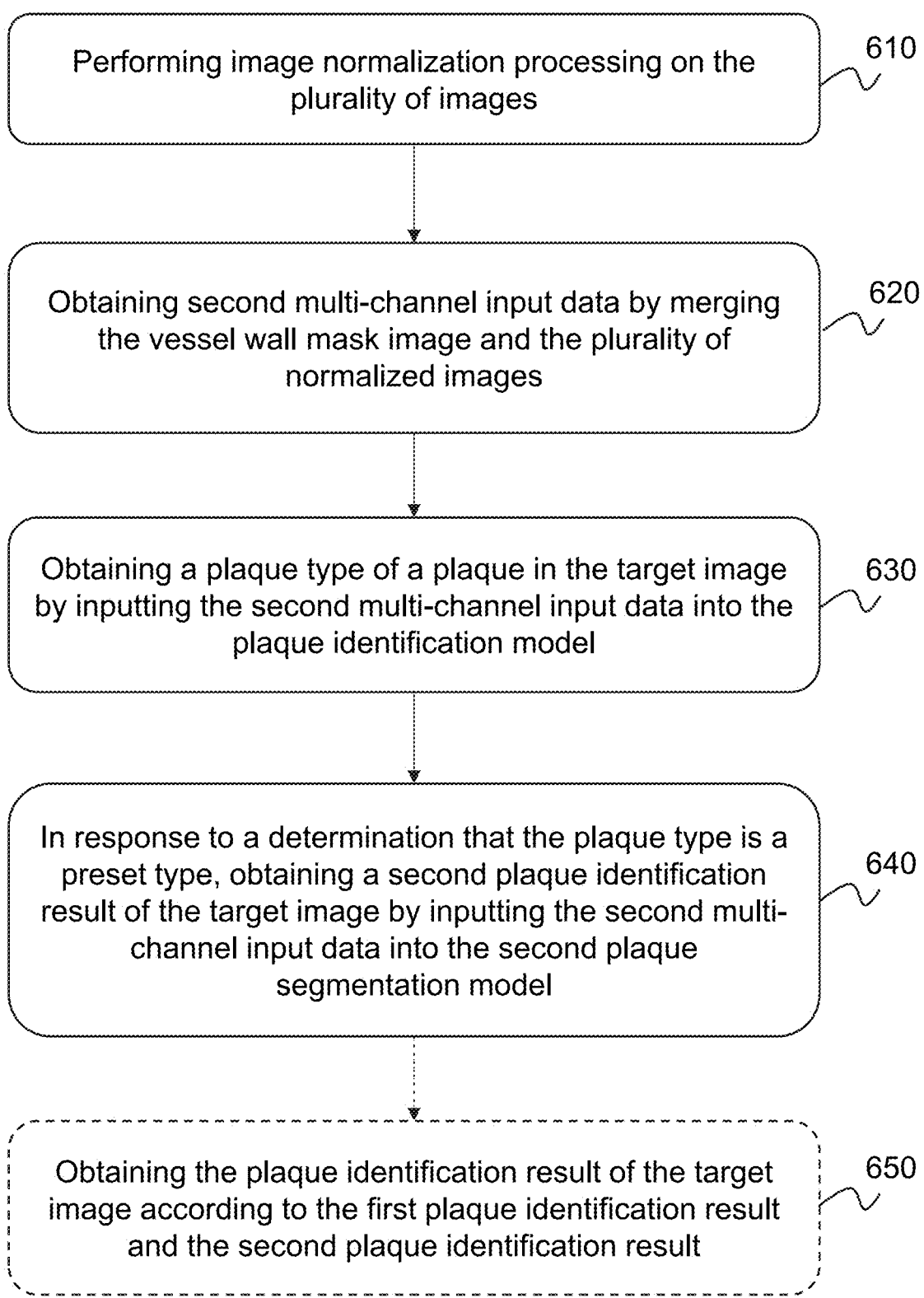
FIG. 6 is a flowchart illustrating an exemplary process for identifying a plaque according to some embodiments of the present disclosure.

FIG. 6 is a flowchart illustrating an exemplary process for identifying a plaque according to some embodiments of the present disclosure. In some embodiments, the process 600 for identifying a plaque may be performed by the processing device 140, the plaque processing system 200 or the computing device 300. For example, the process 600 may be stored in the storage device (e.g., the storage device 150) in a form of a program or an instruction. When the processing device 140 executes the program or the instruction, the process 600 may be implemented. The schematic diagram of operations of the process 600 presented below is intended to be illustrative. In some embodiments, the process 600 may be performed by the plaque identification module 220. In some embodiments, the process may be accomplished with one or more additional operations not described and/or without one or more of the operations herein discussed. Additionally, the order in which the operations of the process 600 illustrated in FIG. 6 and described below is not intended to be limiting.

In 610, image normalization processing may be performed on a plurality of images.

The image normalization processing may include transforming the plurality of images based on one or more algorithms to obtain standard image(s). For example, the image normalization processing may include coordinate centralization, scaling normalization, rotation normalization, etc., for the plurality of images.

In 620, second multi-channel input data may be obtained by merging a vessel wall mask image and the plurality of normalized images.

In some embodiments, the second multi-channel input data may not include the histogram equalized image(s) of the cross-sectional image(s). The histogram equalized image may have enhanced image contrast, which may facilitate locating a plaque. In some embodiments, the histogram equalized image may be not suitable for use in identifying a type of a plaque. Therefore, the histogram equalized image(s) of the cross-sectional image(s) may be not used when the plaque type identification is performed.

In some embodiments, in the second multi-channel input data, an order of the vessel wall mask image and the plurality of cross-sectional images may be that the vessel wall mask image is located in a first position, and the plurality of cross-sectional images are sequentially arranged behind the vessel wall mask image. The order of the vessel wall mask image and the plurality of cross-sectional images may be that the vessel wall mask image is arranged behind the plurality of cross-sectional images. The order of the vessel wall mask image and the plurality of cross-sectional images may be that the vessel wall mask image is arranged adjacent to the target cross-sectional image.

In 630, a plaque type of a plaque in the target image may be obtained by inputting the second multi-channel input data into a plaque identification model.

In some embodiments, the plaque identification model may be a multi-channel identification model, and may process the plurality of images included in the second multi-channel input data to obtain the type of the plaque in the target image.

In some embodiments, the plaque identification model may be a trained identification model for a specific plaque. For example, the plaque identification model may be a calcified plaque identification model, which may be configured to specifically identify the calcified plaque in the target image.

In 640, in response to a determination that the plaque type is a preset type, a second plaque identification result of the target image may be obtained by inputting the second multi-channel input data into a second plaque segmentation model.

The second plaque segmentation model may be configured to segment a plaque of a preset type exclusively. The second plaque identification result may be obtained by specifically identifying the plaque of the preset type in response to a determination that the plaque in the target image is the plaque of the preset type.

In some embodiments, in response to a determination that the plaque in the target image is the plaque of the preset type (e.g., a calcified plaque), the segmentation unit 224 may obtain the second plaque identification result of the target image by inputting the second multi-channel input data into the second plaque segmentation model.

In some embodiments, in response to a determination that the plaque in the target image is not the plaque of the preset type, the segmentation unit 224 may discard the second multi-channel input data, and designate the first plaque identification result as the plaque identification result of the target image.

In 650, a plaque identification result of the target image may be obtained according to a first plaque identification result and the second plaque identification result.

In some embodiments, the segmentation unit 224 may designate the second plaque identification result as the plaque identification result of the target cross-sectional image in response to a determination that the plaque in the target image is the plaque of the preset type. The segmentation unit 224 may designate the first plaque identification result as the plaque identification result of the target image in response to a determination that the plaque in the target image is not the plaque of the preset type.

In some embodiments, the obtaining the plaque identification result of the target image according to the first plaque identification result and the second plaque identification result may include obtaining the plaque identification result of the target image by taking a union set of the first plaque recognition result and the second plaque identification result.

In some embodiments, the plaque of the preset type may be identified by the plaque identification model. The plaque in the target cross-sectional image may be segmented based on the second multi-channel input data using the second plaque segmentation model in response to a determination that the plaque in the target cross-sectional image is of the preset type. For example, the plaque of the preset type may be the calcified plaque. For a situation that a low signal feature of calcification in the images is not conducive to segmentation, if the calcified plaque is identified, a calcification segmentation model may be used to segment the calcified plaque specifically, thereby improving overall accuracy of plaque segmentation.

In some embodiments, the first plaque identification result may include a first plaque identification probability map. The second plaque identification result may include a second plaque identification probability map. The plaque identification module 220 may also determine an average value, a maximum value, or a minimum value of pixel values of each two pixels at a same position in the first plaque identification probability map and the second plaque identification probability map to obtain a plurality of average values, maximum values, or minimum values, and determine the plaque identification result of the target image according to the plurality of average values, maximum values, or minimum values.

In some embodiments, the first plaque identification probability map and the second plaque identification probability map may be determined based on prior information, respectively. For example, the prior information may include distribution information of each pixel value in the images of the normal plaque, the preset plaque (e.g., a calcified plaque). The plaque identification module 220 may perform statistical processing such as determining an average value, a maximum value or a minimum value, etc., for each two pixels at a same position in the first plaque identification probability map and the second plaque identification probability map to obtain statistical information of a plurality of average values, maximum values, or minimum values of each two pixel values. The plaque identification module 220 may perform comparative analysis based on the distribution information of the pixel values in the prior information and the statistical information to determine the plaque identification result of the target image.

In some embodiments of the present disclosure, by performing targeted identification of some plaques of specific types, accuracy of plaque identification can be improved. In addition, by segmenting the plaque through the calcification segmentation model and segmenting the calcified plaque specifically, overall accuracy of plaque segmentation can be improved.

It should be noted that the above description of the process 500 and the process 600 is merely provided for the purpose of illustration, and is not intended to limit the scope of the present disclosure. For persons having ordinary skills in the art, a plurality of variations and modifications may be made to the process 500 and the process 60 under the teachings of the present disclosure. However, those variations and modifications do not depart from the scope of the present disclosure.

FIG. 7 is a flowchart illustrating an exemplary process for analyzing plaque composition according to some embodiments of the present disclosure. In some embodiments, the process 700 for analyzing plaque composition may be performed by the processing device 140, the plaque processing system 200, or the computing device 300. For example, the process 700 may be stored in a storage device (e.g., the storage device 150) in a form of a program or an instruction. When the processing device 140 executes the program or the instruction, the process 700 may be implemented. The schematic diagram of operations of the process 700 presented below is intended to be illustrative. In some embodiments, the process 700 may be performed by the composition analysis module 230. In some embodiments, the process may be accomplished with one or more additional operations not described and/or without one or more of the operations herein discussed. Additionally, the order in which the operations of the process 700 illustrated in FIG. 7 and described below is not intended to be limiting.

In 710, a slice of interest in the plurality of slices in the 3D space may be determined.

In some embodiments, a plurality of images may include a plurality of sequences of images. The plurality of sequences of images may include image information in a same 3D space. The 3D space may include a plurality of slices.

For any target image in the plurality of sequences of images, the composition analysis module 230 may obtain N vessel cross-sectional images on N slices according to a vessel centerline and a target vessel plaque of the target image. N may be an integer greater than 0.

In some embodiments, any sequence of image in the plurality of sequences of images may be or include multi-contrast magnetic resonance images. The plurality of sequences of images may be acquired for a same target object through a plurality of imaging techniques such as a T1-weighted imaging T1WI, a T2-weighted imaging T2WI, a TOF (time of light, based on a time-of-flight principle) imaging, an enhanced T1WI, etc.

In some embodiments, a registration operation may be performed on the plurality of sequences of images, to that the plurality of sequences of images are spatially aligned. For example, after a plurality of images are acquired using a variety of imaging techniques, corresponding points in the plurality of images may be adjusted to be spatially consistent through one or more spatial transformations (i.e., a same part of a same target object may have a same spatial position in the plurality of images).

Figure 11:
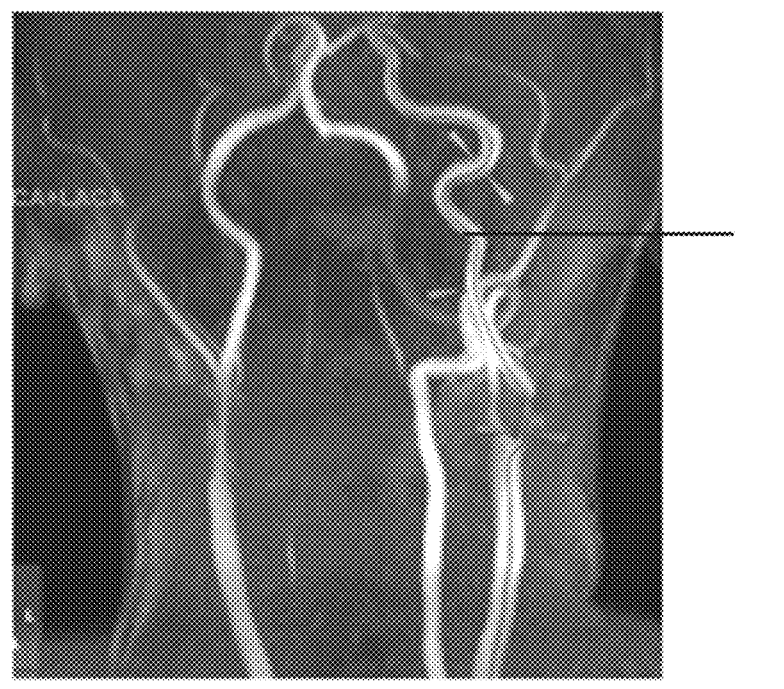
FIG. 11 is a schematic diagram illustrating an exemplary plaque composition analysis according to some embodiments of the present disclosure.

In some embodiments, the composition analysis module 230 may determine, according to one or more target images in a plurality of sequences of images, a vessel centerline (e.g., as shown in FIG. 11) and a target vessel plaque in the plurality of sequences of images. For example, the vessel centerline in the plurality of sequences of images may be obtained by performing a vessel centerline extraction operation on one or more target images using a trained neural network for extracting vessel centerlines. Alternatively, the vessel centerline in the plurality of sequences of images may be marked by a user through a manual operation on a terminal interface. In the same way, the vessel plaque in the plurality of sequences of images may be obtained by performing vessel plaque extraction on one or more target images through a trained neural network for extracting vessel plaques. The target vessel plaque may be any vessel plaque among the detected vessel plaques or may be identified by a user or the plaque processing system 200. Alternatively, after the user determines starting and/or ending points of the vessel plaque in the terminal interface, the target vessel plaque may be drawn. The above is merely examples of extracting the vessel centerline and the target vessel plaque.

After obtaining the vessel centerline and the target vessel plaque, for any target image, the composition analysis module 230 may determine, on the vessel centerline and in a region corresponding to the target vessel plaque (hereinafter referred to as a plaque region), N points, and reconstruct target images based on the N points. For any target image, N vessel cross-sectional images may be obtained.

For example, the composition analysis module 230 may determine a central point P0 of the plaque region, obtain k points in a front-rear direction of the vessel with a step size of $\lambda$ ($\lambda$ may be a preset value) by taking the central point P0 as a midpoint (i.e., take a total of (2k+1) points from the plaque region), and reconstruct a corresponding vessel cross-sectional image. For example, taking the point P0 as an example, the vessel cross-sectional image may be reconstructed in the X-Y axis plane of P0. Similarly, (2k+1) vessel cross-sectional images may be obtained.

In some embodiments, the composition analysis module 230 may obtain a region of interest image corresponding to the plurality of sequences of images by performing segmentation processing according to the plurality of sequences of images. A slice where the region of interest image is located may be the slice of interest. The region of interest image may be configured to characterize the slice of interest. In addition, in the present disclosure, the region of interest image may also be referred to as an ROI image for short.

In some embodiments, the composition analysis module 230 may obtain the ROI image corresponding to the plurality of sequences of images by performing segmentation processing on the plurality of sequences of images through a trained neural network for generating ROI images. The ROI image may include a reference region for comparison with the vessel plaque region, e.g., a sternocleidomastoid muscle region.

In 720, for each sequence of images in the plurality of sequences of images, a plurality of target slice images corresponding to a plurality of target slices where the target plaque is located may be generated based on the slice of interest, a vessel centerline of a vessel in the 3D space, and a target plaque of the vessel. More descriptions of determining the target plaque may be found in FIG. 9 and descriptions thereof.

In some embodiments, the processing device 140 may determine a plurality of reference slices on both sides of the slice of interest respectively along the vessel centerline and within a range of the target plaque, designate the slice of interest and the plurality of reference slices as the plurality of target slices, and for each sequence of images in the plurality of sequences of images, generate the plurality of target slice images corresponding to the plurality of target slices where the target plaque is located.

In some embodiments, the processing device 140 may take the slice of interest as a starting slice, and determine the plurality of reference slices on both sides of the slice of interest along the vessel centerline based on a preset step size. For example, at a point P where the vessel centerline intersects the starting slice, within the range of the target plaque, n slices of interest on both sides of the slice of interest along the vessel centerline with a step size of $\lambda$ along the point P (i.e., totally 2n slices of interest) may be obtained. The obtained 2n slices of interest may be designated as the reference slices.

In 730, a composition probability map of at least one composition of a plaque on each slice of the plurality of target slices may be determined according to at least part of the plurality of target slice images corresponding to the plurality of sequences of images. In some embodiments, the composition probability map of the target vessel plaque on the $i^{th}$ slice may be determined according to the target vessel cross-sectional image(s) on the $i^{th}$ slice.

In some embodiments, the vessel cross-sectional image on the $i^{th}$ slice may be determined as the target vessel cross-sectional image. The composition probability map of the target vessel plaque on the $i^{th}$ slice may be determined through the target vessel cross-sectional image in the plurality of sequences of images. The composition probability map may be configured to represent a probability that each position in the target vessel plaque on the $i^{th}$ slice is a composition to be detected.

For example, the composition probability map of the target vessel plaque on the $i^{th}$ slice may be obtained by performing statistical analysis on the target vessel cross-sectional images. For example, the composition probability map of the target vessel plaque on the $i^{th}$ slice may be obtained by performing statistical analysis processing on the target vessel cross-sectional images through the trained neural network for generating the composition probability map. Alternatively, a reference region of the vessel plaque (e.g., a sternocleidomastoid muscle region) may also be obtained, and a signal level in the target vessel cross-sectional images and a signal level in the reference region may be compared and analyzed. A probability that each pixel is the composition to be detected may be determined according to the obtained comparison and analysis result, and then the corresponding composition probability map may be obtained. The process of generating the composition probability map will not be limited specifically in the present disclosure.

In some embodiments, a composition probability map of at least one composition of the plaque on the each slice of the plurality of target slices may be determined based on prior distribution, the plurality of intensity relative maps corresponding to the at least part of the target slice images, and a preset probability function.

In some embodiments, for any of the target images, the intensity relative image may be obtained according to the target vessel cross-sectional image and a statistical image corresponding to the target image on the $i^{th}$ slice. The intensity relative map may be configured to characterize a relative result of the signal intensity between the target vessel cross-sectional image and the statistical image. In the present disclosure, the intensity relative image may referred to as the intensity relative map.

In some embodiments, the composition analysis module 230 may extract, based on at least one sequence of images in the plurality of sequences of images, a region of interest. For each of the plurality of target slice images, a plurality of pixels in the region of interest may be extracted from the each of the plurality of target slice images, a statistical value of the plurality of pixels may be determined, and the intensity relative map corresponding to the each of the at least part of the plurality of target slice images may be determined based on the each of the plurality of target slice images and the statistical value.

After the ROI image is obtained, the composition analysis module 230 may obtain a statistical image corresponding to each target image by performing statistical processing on the signals in a region corresponding to the ROI image (hereinafter referred to as a reference region) in each target image through the ROI image. For example, the statistical image corresponding to each target image may be obtained by performing statistical processing such as determining a mean value, a median value, etc., on the ROI image and the reference region.

After the statistical image corresponding to the target image is obtained, the composition analysis module 230 may perform a signal comparison processing on the target vessel cross-sectional image(s) on the $i^{th}$ slice and the statistical image, and obtain an intensity relative image according to the signal comparison result. For example, the signal comparison processing may be a process of dividing each pixel in the target vessel cross-sectional image and each pixel in the statistical image, or may be a process of dividing each pixel in the statistical image and each pixel in the target vessel cross-sectional image. The process of dividing each pixel in the target vessel cross-sectional image and each pixel in the statistical image may be taken as an example in the present disclosure.

After the intensity relative image of each target object (e.g., a target plaque) on the $i^{th}$ slice is obtained, the composition probability map of the target vessel plaque on the $i^{th}$ slice may be obtained by performing the composition probability analysis processing through the prior information of the composition distribution and the intensity relative image of each target object on the $i^{th}$ slice.

In some embodiments, a prior distribution may be obtained. The prior distribution may be or include a preset prior distribution table.

For example, main compositions in a vessel plaque may be judged with an adjacent muscle tissue signal as a reference standard. Exemplary composition distribution prior information may be the composition prior distribution table T below. Values in the composition prior distribution table T may include: +(high signal), 0 (equal signal), –(low signal).

TABLE 1

| Exemplary Composition Prior Distribution Table T | | | | |
|---|---|---|---|---|
| Composition | T1WI | T2WI | TOF | Enhanced T1WI |
| Lipid necrosis core | 0/+ | –/0 | 0 | – |
| Hemorrhage | + | 0/+ | + | – |
| Calcification | – | – | – | – |
| Loose interstitium | –/0 | + | 0 | + |
| Fibrous cap rupture-niche | – | – | – | – |

According to the composition prior distribution table T, a relative distribution sequence of each composition on different target images may be obtained, such as: a relative distribution sequence of calcification may be (–, –, –, –). A probability that each pixel in the target vessel cross-sectional image belongs to each composition may be determined by a preset probability function P. Input information of the probability function P may be the prior distribution table T and the intensity relative image of each target image on the $i^{th}$ slice, and output information may be the probability that each pixel belongs to each composition. For any composition, the composition probability map corresponding to the composition may be obtained according to the obtained probability that each pixel belongs to the composition.

For example, any intensity relative image may be ternary-valued through thresholds. For example, if a pixel value of a pixel is in a range of (0, 0.8), the pixel value may be converted into a signal "–". If a pixel value of a pixel is in a range of (0.8, 1.2), the pixel value may be converted into a signal "0". If a pixel value of a pixel is in a range of (1.2, infinite), the pixel value may be converted into a signal "+". After each intensity relative map is subjected to the above conversion processing, each pixel may correspond to a ternary-valued sequence in the prior distribution table T. Further, for any composition, a distance from the ternary-valued sequence to a relative distribution sequence corresponding to the composition (e.g., calcification) may be calculated. The distance calculation may include a chessboard distance measurement, an Euler distance measurement, etc., which will not be specifically limited in the present disclosure.

After the distance from the ternary-valued sequence corresponding to each pixel to the relative distributed sequence corresponding to the composition is obtained, the distance corresponding to each pixel may be converted into a probability. For example, the distance may be converted to the probability by the probability function. The probability function may make the probability be 1 when the distance is 0. The larger the distance, the smaller the probability. Probabilities for all pixels in a vessel wall interior (e.g., a region between the contour of the vessel wall and the contour of the vessel lumen may be determined as the vessel wall interior) may be calculated based on the probability function. A probability that a pixel outside the vessel wall belongs to the composition may be determined to be 0. Probabilities that a plurality of pixels belong to the composition may constitute the composition probability map of the target vessel plaque on the $i^{th}$ slice.

In some embodiments, the region of interest may be obtained by a fourth segmentation model. An ROI image corresponding to the plurality of sequences of images may be obtained by segmenting the plurality of sequences of images through the fourth segmentation model. In some embodiments, a trained fourth segmentation model may be obtained by training an initial fourth segmentation model according to a preset training set.

In some embodiments, the training set may include a plurality of second sample groups. Each of the second sample groups may include a plurality of sequences of sample images and a label thereof. The label may be a labelled region of interest image corresponding to the plurality of sequences of sample images.

In some embodiments, the second training set may be preset. The label may be pre-labeled in at least one sample image of the plurality of sequences of sample images according to prior knowledge. In some embodiments, a predicted region of interest image may be obtained by inputting the at least one sample image in the plurality of sequences of sample images into an initial fourth segmentation model, and a predicted loss of the initial fourth segmentation model may be determined according to the predicted region of interest image and the label. Model parameters of the initial fourth segmentation model may be adjusted when the predicted loss does not satisfy a training requirement (for example, the predicted loss is greater than a preset loss threshold), model training may be terminated until the predicted loss of the initial fourth segmentation model satisfies the training requirement (for example, the predicted loss is smaller than or equal to the preset loss threshold), and the trained fourth segmentation model may be obtained.

In the method for composition analysis provided in some embodiments of the present disclosure, since the high and low features of the signals of different compositions on different sequences of images and in the reference region have prior distributions, that is, a composition probability map of each composition may be constructed using the prior distribution of each composition as a constraint condition, and then composition analysis may be performed automatically using the composition probability map as a constraint condition, which can further improve accuracy and efficiency of composition analysis.

In 740, a composition distribution image of the at least one composition of a plaque on the slice of interest may be determined according to the plurality of sequences of images, and the composition probability map of the at least one composition corresponding to the each slice.

In some embodiments, the composition distribution image corresponding to the target vessel plaque on the $i^{th}$ slice may be obtained according to the composition probability map and the target vessel cross-sectional image(s) on the $i^{th}$ slice.

In some embodiments, a composition distribution image corresponding to the target vessel plaque on the $i^{th}$ slice may be obtained by performing composition analysis processing through the composition probability map and the target cross-sectional image on the $i^{th}$ slice. The composition distribution image may be configured to represent composition(s) corresponding to each position in the target vessel plaque. For example, different colors may be used to represent different compositions in the composition distribution image. As another example, the composition may include at least one of the compositions such as lipid necrosis core, calcification, hemorrhage, loose interstitium, fibrous cap rupture-niche, etc. Different compositions may be identified with different colors in the composition distribution image.

In some embodiments, the composition distribution image corresponding to the target vessel plaque on the $i^{th}$ slice may be obtained by performing composition analysis processing on the composition probability map and the target vessel cross-sectional image(s) on the $i^{th}$ slice through the trained neural network. Similarly, the composition distribution images corresponding to the target vessel plaque on n slices may be obtained.

In some embodiments, the vessel cross-sectional image may include at least one of a target vessel cross-sectional image or a histogram equalized image obtained by performing histogram equalization processing on the target vessel cross-sectional image.

In some embodiments, the histogram equalized image corresponding to the each target vessel cross-sectional image may be obtained by performing the histogram equalization processing on each target vessel cross-sectional image, respectively. The composition distribution image corresponding to the target vessel plaque on the $i^{th}$ slice may be obtained by performing composition analysis processing according to the target vessel cross-sectional image and/or histogram equalized image of each target image on the $i^{th}$ slice and the composition probability map.

Based on the method for composition analysis provided in some embodiments of the present disclosure, since the histogram equalization image may strengthen the image contrast, performing the composition analysis in combination with the histogram equalization image can further improve accuracy of the composition analysis, thereby obtaining a more accurate composition distribution image.

In some embodiments, the composition analysis module 230 may determine, based on at least one sequence of images in the plurality of sequences of images, a distance field map of the vessel. More descriptions regarding the distance field map of the vessel may be found in FIG. 8 and descriptions thereof.

In some embodiments, the composition analysis module 230 determine, according to the plurality of sequences of images, the composition probability map of the at least one composition corresponding to the each slice, the intensity relative map corresponding to the each of the at least part of the plurality of target slice images, the histogram equalized image corresponding to the each of the at least part of the plurality of target slice images, and the distance field map, the composition distribution image of the at least one composition of the plaque on the slice of interest.

In some embodiments, the composition analysis module 230 may obtain an associated analysis image corresponding to the target vessel plaque according to each target image and/or the target vessel cross-sectional image(s) on the $i^{th}$ slice. The associated analysis image may include at least one of a distance field image corresponding to the target vessel cross-sectional image, or an intensity relative image corresponding to each target vessel cross-sectional image.

The composition analysis module 230 may obtain the composition distribution image corresponding to the target vessel plaque on the $i^{th}$ slice according to the composition probability map, the vessel cross-sectional image(s) on the $i^{th}$ slice, and the associated analysis image.

In some embodiments, a segmented image of the vessel lumen and the vessel wall of the vessel may be obtained by analyzing the target vessel cross-sectional image(s) on the $i^{th}$ slice, and the distance field image may be obtained according to distances from each pixel to the contour of the vessel lumen and the contour of the vessel wall. That is, the distance field image may be used to represent distances from each pixel to the vessel lumen and the vessel wall.

In some embodiments, a reference region of the target vessel plaque may be obtained through each target image. The reference region may be an ROI. For example, an ROI image may be obtained by segmenting each target image through a trained neural network for generating the ROI image. Then, an intensity relative image corresponding to each target vessel cross-sectional image may be obtained by comparing a signal level of each target vessel cross-sectional image with that of the ROI image respectively. That is, the intensity relative image may be used to characterize a signal intensity comparison result between the target vessel cross-sectional image and the ROI image.

After the intensity relative map and/or the distance field map are obtained, the composition distribution image corresponding to the target vessel plaque on the $i^{th}$ slice may be obtained by performing composition analysis processing according to the intensity relative image and/or the distance field image, the composition probability map, and the vessel cross-sectional image(s) on the $i^{th}$ slice.

In some embodiments of the present disclosure, a position prior may be added to the composition analysis process by performing composition analysis in combination with the distance field image, which may assist in composition segmentation. For example, a fibrous cap is a region close to the lumen of the vessel. A distance between each position and the lumen of the vessel may be obtained through the distance field image, so as to judge whether the distance belongs to the fibrous cap to a certain extent according to the distance. Using the intensity relative image for composition analysis may simulate comparison process with the user's naked eyes, which can avoid a subjective difference of the comparison with the user's naked eyes. Therefore, the composition analysis may be performed using the distance field map and/or the intensity relative image can further improve accuracy of the composition analysis, so as to obtain a more accurate composition distribution image.

In some embodiments, the composition analysis module 230 may obtain a composition analysis result of at least one part of the target plaque of the vessel by performing a statical analysis on the composition distribution image of the at least one composition of the plaque on the slice of interest.

In some embodiments, after the composition distribution image(s) of the target plaque on N slices are obtained, a composition analysis result of the target plaque may be obtained by performing the statistical analysis on the N composition distribution images. The statistical analysis may include an analysis operation such as a maximum area analysis of each composition, a volume analysis of each composition, a volume ratio analysis of each composition, etc. Accordingly, the composition analysis result may include a result such as a maximum area of each composition, a volume of each composition, and a volume ratio of each composition, etc.

For example, for any composition, a count of pixels belongs to the composition in the composition distribution image on each slice may be determined, the area of the composition on each slice may be obtained, and the maximum area of the composition in the target vessel plaque may be determined. Further, the area of the composition on each slice may be summed up, and the volume of the composition in the target vessel plaque may be obtained. Furthermore, the volume ratio of the composition may be obtained by calculating a ratio of the volume of the composition in the target vessel plaque to a total volume of the target vessel plaque.

In the method for composition analysis provided in some embodiments of the present disclosure, the statistical analysis processing may be performed by automatically generating the composition distribution image in the target vessel plaque to obtain the statistical analysis result of each composition in the target vessel plaque, which can avoid an influence of a subjective factor when comparing and analyzing with naked eyes, and improve accuracy and efficiency of statistical analysis.

In some embodiments, the composition analysis module 230 may input the plurality of sequences of images, the composition probability map of the at least one composition corresponding to the each slice, the intensity relative map corresponding to the each of the at least part of the plurality of target slice images, the histogram equalized image corresponding to the each of the at least part of the plurality of target slice images, and the distance field map into a third segmentation model. The composition distribution image of the at least one composition of the plaque on the slice of interest may be obtained through the processing of the third segmentation model.

In some embodiments, the composition analysis module 230 may obtain, according to the composition probability map and the target vessel cross-sectional image(s) on the $i^{th}$ slice, a composition distribution image corresponding to the target vessel plaque on the $i^{th}$ slice through a trained composition analysis network. The method for composition analysis may also include: obtaining the composition analysis network by training an analysis network according to a preset first training set. The composition analysis network may be referred to as the third segmentation model.

The first training set may include a plurality of first sample groups. The first sample group may include a plurality of sequences of sample images, sample vessel cross-sectional images corresponding to the plurality of sequences of sample images on N slices, and labelled composition distribution images of sample vessel cross-sectional images of each slice.

In some embodiments, in a process of training the composition analysis network, the first training set may be preset. The first training set may include the plurality of first sample groups. The first sample group may include a plurality of sequences of sample images, sample vessel cross-sectional images corresponding to the plurality of sequences of sample images on N slices, and labelled composition distribution images of sample vessel cross-sectional images of each slice. For example, each composition of the target vessel plaque in the sample vessel cross-sectional image of each slice may be determined in advance based on the prior knowledge, and each composition may be labelled to obtain a labelled composition distribution image.

In some embodiments, input information of the composition analysis network may be constructed according to the plurality of sequences of sample images and/or the vessel cross-sectional images corresponding to the plurality of sequences of sample images on N slices. The input information may include at least one of a sample composition probability map corresponding to the $i^{th}$ slice, a sample vessel cross-sectional image corresponding to the plurality of sequences of sample images on the $i^{th}$ slice, or a sample histogram equalized image corresponding to each sample vessel cross-sectional image, or may also include at least one of a plurality of sample intensity relative images and a plurality of sample distance field images corresponding to the plurality of sequences of sample images on the $i^{th}$ slice.

Processes for determining the sample composition probability map, the histogram equalized image, the sample intensity relative image and the sample distance field image may be found in the relevant descriptions of the above embodiments, which will not be repeatedly herein. In some embodiments, the sample composition probability map, the histogram equalized image, the sample intensity relative image and the sample distance field image may be obtained by image processing according to the sample group, or may also be included in the sample group after being obtained by image processing in advance, which will not be specifically limited in the present disclosure.

In some embodiments, the composition analysis module 230 may obtain a predicted composition distribution image by inputting the above input information into the analysis network for composition analysis. The analysis network may be a deep segmentation network. A predicted loss of the analysis network may be determined according to the predicted composition distribution image and the labelled composition distribution image. Network parameters of the analysis network may be adjusted when the predicted loss does not satisfy a training requirement (for example, the predicted loss is greater than a preset loss threshold), network training may be stopped until the predicted loss of the analysis network satisfies the training requirement (for example, the predicted loss is smaller than or equal to the preset loss threshold), and the trained analysis network may be obtained.

In the method for composition analysis provided in some embodiments of the present disclosure, the composition distribution image of the target vessel plaque may be obtained by performing the composition analysis processing through the composition analysis network, which can avoid an influence of subjectivity when performing composition analysis with human eyes, make the composition analysis result more objective and accurate, and improve accuracy and efficiency of composition analysis.

In some embodiments of the present disclosure, by automatically obtaining the reference region and the ROI and obtaining the relative intensity map of the signal values of the vessel wall region and the reference region in the plurality of sequences of images, a relationship of the signal difference between the vessel wall region and the reference region may be quantificationally compared, which can avoid errors caused by positioning using the doctor's eyes and subjective judgment. The composition analysis result of each composition of the plaque may be obtained by automatically segmenting each composition of the plaque using the deep learning method based on a prior feature such as the original image, the intensity relative image, the distance field image, the composition probability map, etc. The statistical information such as a volume, a volume ratio, and a distribution position of each composition of the plaque may be obtained based on the analysis result of each composition, which can improve accuracy and efficiency of composition analysis.

It can be understood that, although the operations in the flowcharts involved in the above embodiments are displayed in sequence according to the arrows, these operations are not necessarily executed sequentially in the order indicated by the arrows. The operations are not strictly executed in the order unless explicitly stated herein. The operations may be executed in other orders. Moreover, at least a part of the operations in the flowcharts involved in the above embodiments may include a plurality of operations or a plurality of stages. The plurality of operations or stages are not necessarily performed at a same time, but may be performed at different times. These operations or stages are also not performed necessarily in order, but may be performed alternately or alternatively with other operations or at least a part of the operations or stages in the other operations.

FIG. 8 is a flowchart illustrating an exemplary process for determining a distance field map according to some embodiments of the present disclosure. In some embodiments, the process 800 for determining the distance field map may be performed by the processing device 140, the composition analysis module 230, or the computing device 300. For example, the process 800 may be stored in a storage device (e.g., the storage device 150) in a form of a program or an instruction. When the processing device 140 executes the program or the instruction, the process 800 may be implemented. In some embodiments, as shown in FIG. 8, the process 800 may include the following operations.

In 810, a segmentation result of a vessel lumen and a vessel wall of the vessel may be obtained by inputting one or more target slice images corresponding to the at least one sequence of images into a second segmentation model.

In some embodiments, the composition analysis module 230 may obtain a segmented image of the vessel lumen and the vessel wall of the plurality of sequences of images on the $i^{th}$ slice according to the target vessel cross-sectional image(s) on the $i^{th}$ slice. For example, the composition analysis module 230 may obtain a segmented image of the vessel lumen and the vessel wall of the plurality of sequences of images on the $i^{th}$ slice by performing segmentation processing according to the target vessel cross-sectional image(s) on the $i^{th}$ slice. A vessel lumen region and a vessel wall region may be identified in the segmentation image of the vessel lumen and the vessel wall.

In some embodiments, the segmentation result of the vessel lumen and the vessel wall of the plurality of sequences of images on the $i^{th}$ slice may be obtained by performing segmentation processing on the target vessel cross-sectional image(s) on the $i^{th}$ slice through the trained second segmentation model for segmentation of the vessel lumen and the vessel wall. Alternatively, a user may draw the segmentation result of the vessel lumen and the vessel wall on the $i^{th}$ slice of the plurality of sequences of images through a manual operation on a terminal interface.

In 820, a contour of the vessel lumen and a contour of the vessel wall may be determined based on the segmentation result of the vessel lumen and the vessel wall. In some embodiments, the composition analysis module 230 may determine the contour of the vessel lumen and the contour of the vessel wall based on the vessel lumen region and the vessel wall region identified in the segmentation image of the vessel lumen and the vessel wall according to the segmentation result of the vessel lumen and the vessel wall.

In 830, a first distance and a second distance from each pixel in the vessel wall of the vessel to the contour of the vessel lumen and the contour of the vessel wall may be determined respectively. In some embodiments, the composition analysis module 230 may determine the first distance from each pixel in the vessel wall to the contour of the vessel lumen and the second distance from each pixel in the vessel wall to the contour of the vessel wall in the segmentation image of the vessel lumen and the vessel wall.

After the segmented image of the vessel lumen and the vessel wall is obtained, for each pixel inside the interior of the vessel wall (a region between the contour of the vessel wall and the contour of the vessel lumen may be determined as an interior of the vessel wall), the compositional analysis module 230 may determine the first distance from the each pixel to the contour of the vessel lumen and the second distance from the each pixel to the contour of the vessel wall. A distance field result corresponding to each pixel may be obtained by performing the distance field result calculation according to the first distance and the second distance corresponding to each pixel in the vessel wall. The distance field result may be configured to characterize a distance from the pixel to the contour of the vessel lumen and the contour of the vessel wall.

In 840, the distance field map may be determined based on a distance field mapping function, a plurality of first distances and a plurality of second distances corresponding to a plurality of pixels in the vessel wall of the vessel.

In some embodiments, the composition analysis module 230 may determine, based on the distance field mapping function, the plurality of first distances and the plurality of second distances corresponding to the plurality of pixels in the vessel wall of the vessel, the distance field map.

For example, distance field results may be determined based on the first distance and the second distance of each pixel using a distance field mapping function. The distance field mapping function may be identified as $f(x1, x2)$. when $x1 \le \sigma f(x1, x2)=1$, where $0 \le \sigma < x1+x2$, is a hyperparameter. When $x1 > \sigma$, $f(x1, x2)=g(t)$, where $t=|x1 \ \sigma|/(x1+x2)$, $g(t)$ is a decreasing function, and $g(0)=1$. Further, the distance field map may be determined according to the distance field result corresponding to each pixel.

In some embodiments of the present disclosure, since the distance field image may be configured to characterize the distances from the pixel to the contour of the vessel lumen and the contour of the vessel wall, the prior of each position may be added through the distance field image, which may assist in composition segmentation. Therefore, composition analysis combined with the distance field image can further improve accuracy and efficiency of composition analysis.

FIG. 9 is a flowchart illustrating an exemplary process for determining a target plaque according to some embodiments of the present disclosure. In some embodiments, the process 900 for determining a target plaque may be performed by the processing device 140, the composition analysis module 230, or the computing device 300. For example, the process 900 may be stored in a storage device (e.g., the storage device 150) in a form of a program or an instruction. When the processing device 140 executes the program or the instruction, the process 900 may be implemented. In some embodiments, as shown in FIG. 9, the process 900 may include the following operations.

In 910, for the centerline point of interest, a target image may be obtained by determining, from at least one sequence of images in the plurality of sequences of images, a cross-sectional image including the centerline point of interest and perpendicular to the vessel centerline. Relevant descriptions may be found in FIG. 5 and descriptions thereof.

In 920, a plurality of reference centerline points on both sides of the centerline point of interest on the vessel centerline may be determined, and a cross-sectional image corresponding to each of the plurality of reference centerline points may be obtained.

For example, the composition analysis module 230 may obtain n reference centerline points (i.e., totally 2n+1 reference centerline points including point P) on both sides of the centerline point of interest P on the vessel centerline based on a preset step size ($\lambda$ may be a preset value). Further, a cross-sectional image corresponding to each of the 2n+1 reference centerline points may be obtained.

In 930, an image set corresponding to the target image may be obtained according to the target image and the plurality of cross-sectional images corresponding to the plurality of reference centerline points. The image set may include a plurality of image layers. The target image may be one of the plurality of image layers.

For example, after obtaining the cross-sectional image corresponding to each of the 2n+1 reference centerline points, the composition analysis module 230 may further obtain an image set including the 2n+1 cross-sectional images, and the target image may be one of the image set.

In 940, a plaque identification result of the target image may be obtained by inputting the plurality of images and the plurality of histogram equalized images corresponding to the plurality of images into a trained segmentation model.

In some embodiments, the composition analysis module 230 may obtain the histogram equalized image corresponding to each image layer in the image set by performing histogram equalization processing on the each image layer. More descriptions regarding the histogram equalization processing and the histogram equalized image may be found in FIG. 5 and descriptions thereof.

In some embodiments, the composition analysis module 230 may obtain at least one part of the target plaque by inputting the image set and the plurality of histogram equalized images corresponding to the image set into a first trained segmentation model. Relevant descriptions regarding the first segmentation model may be found in FIG. 5 or FIG. 6 and descriptions thereof.

In some embodiments, the composition analysis module 230 may further determine the target plaque based on the at least one part of the target plaque corresponding to the each of the at least two centerline points of interest. For example, the composition analysis module 230 may determine the target plaque by splicing at least one part of the plurality of the target plaques, etc.

In the method for composition analysis provided in some embodiments of the present disclosure, the composition distribution image of the target vessel plaque may be obtained by automatically extracting the ROI through the segmentation network (e.g., the second segmentation model, the third segmentation model) for signal level comparison, and composition analysis, which can avoid an influence of subjectivity in composition analysis with human eyes, and make the composition analysis result more objective and accurate, thereby improving accuracy and efficiency of composition analysis.

In order for those skilled in the art to better understand the method for plaque composition analysis of the embodiments of the present disclosure, the embodiments of the present disclosure will be illustrated below through the specific examples.

In some embodiments, after the plurality of sequences of images are obtained, image registration may be performed, so that each image in the plurality of sequences of images may achieve spatial alignment (the images mentioned below may be registered images).

The extraction of the vessel centerline based on the plurality of sequences of images may include, but is not limited to, traditional algorithm-based or deep learning-based centerline extraction methods based on a single image or the plurality of sequences of images, or a manual extraction method. The detection of vessel plaque based on the plurality of sequences of images may include, but is not limited to traditional algorithm-based or deep learning-based plaque extraction methods based on a single image or the plurality of sequences of images, or a manual extraction method of manually determining the starting and ending points of the plaque on the centerline.

The following operations are performed within a range of the target vessel plaque based on the above vessel plaque detection result.

In a vessel centerline point P0 of an image Si in the plurality of sequences of images, k points with a step size of $\lambda$ on the vessel centerline may be obtained along a front-rear direction of the vessel. Taking the obtained (2k+1) points as centers, (2k+1) vessel cross-sectional images Ii may be reconstructed.

Multi-channel 3D input information may be constructed based on at least one image in the above plurality of sequences of images, and the ROI image may be obtained by inputting the input information into the trained segmentation model.

The statistical image Vi of each ROI in the image Si may be calculated using the ROI image and the image Si (the statistical image may be obtained through mean value or median value calculations), and the intensity relative image Di corresponding to the image Si may be obtained by dividing each pixel in the vessel cross-sectional image Ii and each pixel in the Vi.

For the above vessel cross-sectional image Ii, the segmented image W1 of the vessel lumen and the vessel wall corresponding to the vessel cross-sectional image may be obtained using the trained segmentation model or manual editing by the user. In the segmented image W1 of the vessel lumen and the vessel wall, a background, the vessel lumen, and the vessel wall may be represented by different values, respectively.

The contour L1 of the vessel lumen and the contour L2 of the vessel wall may be obtained from the segmentation image W1 of the vessel lumen and the vessel wall. The distance x1 and the distance x2 from each pixel in the vessel wall in the segmentation image W1 of the vessel lumen and the vessel wall to the contour L1 of the vessel lumen and the contour L2 of the vessel wall may be calculated. The distance field result $f(x1, x2)$ of a current pixel may be obtained by using the given distance field mapping function f, and the distance field image F may be formed according to the distance field result corresponding to each pixel.

The relative distribution sequence of each composition on different images in the plurality of sequences of images may be obtained using the composition prior distribution table T. The probability that a pixel belongs to a composition may be obtained by performing probability conversion on the composition prior distribution table T and each intensity relative image Di according to the given probability prior function P. The probabilities for all pixels of the vessel wall may be calculated based on the probability prior function P. The probability of a pixel outside the vessel wall belongs to a certain composition may be 0. The composition probability map Pi of a certain composition may be formed according to the probabilities of all pixels belong to a the composition.

A histogram equalized image Hi corresponding to each vessel cross-sectional image Ii may be obtained by performing histogram equalization on each of the above vessel cross-sectional images Ii.

Figure 10A:
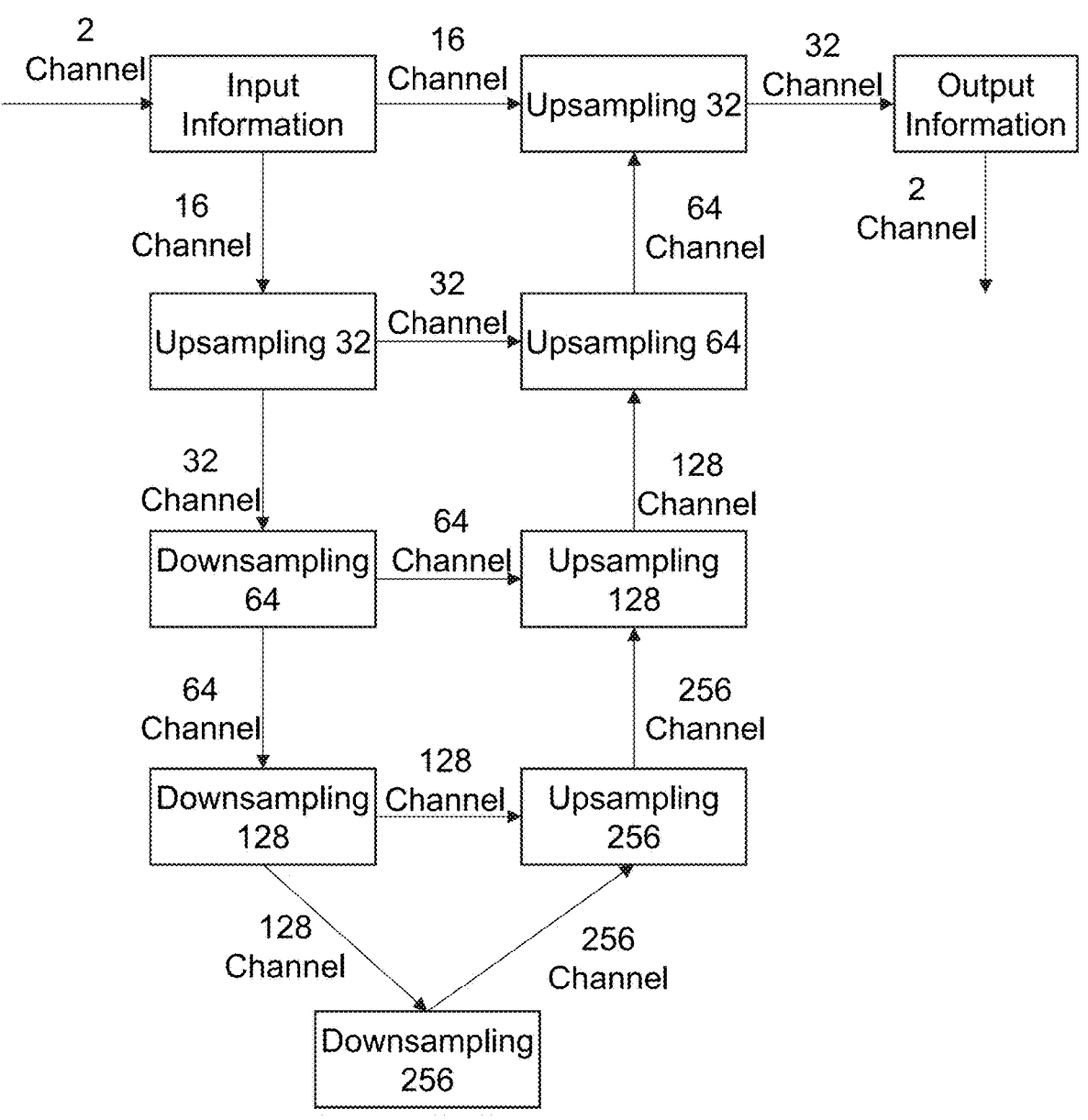
FIG. 10A is a schematic diagram illustrating an exemplary plaque composition analysis process according to some embodiments of the present disclosure.
Figure 10B:
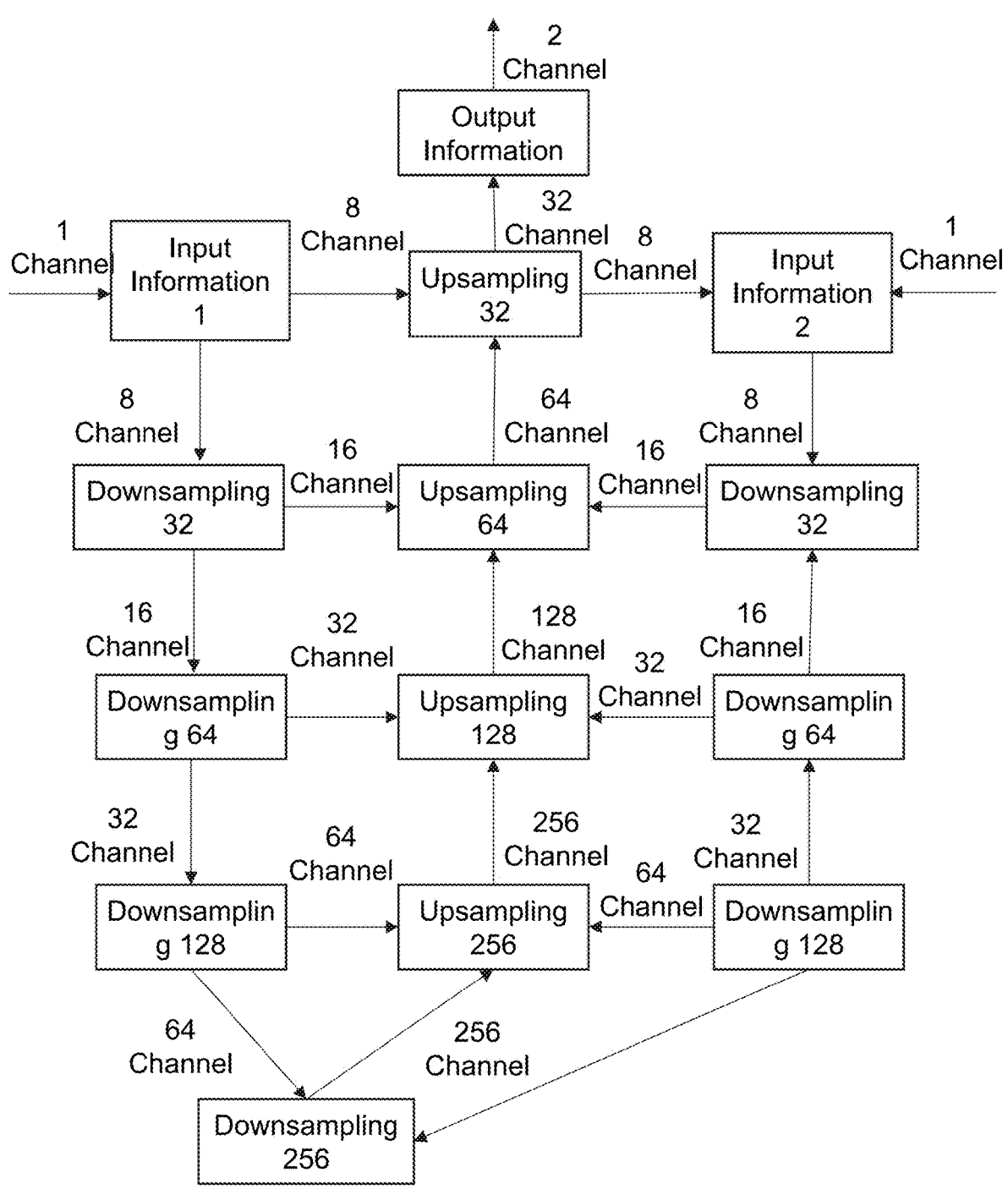
FIG. 10B is a schematic diagram illustrating an exemplary plaque composition analysis process according to some embodiments of the present disclosure.

The composition distribution image may be obtained by inputting the Ii, Di, Hi, F, Pi into the trained composition analysis network (for example, a network structure of the composition analysis network may be found in FIG. 10A or FIG. 10B) as multi-channel or multi-branch input. The statistical information of each composition in the target vessel plaque, such as the maximum area, the volume, the volume ratio, etc., may be obtained through statistical analysis made on the compositions of the target vessel plaque based on the above composition distribution image.

Figure 12:
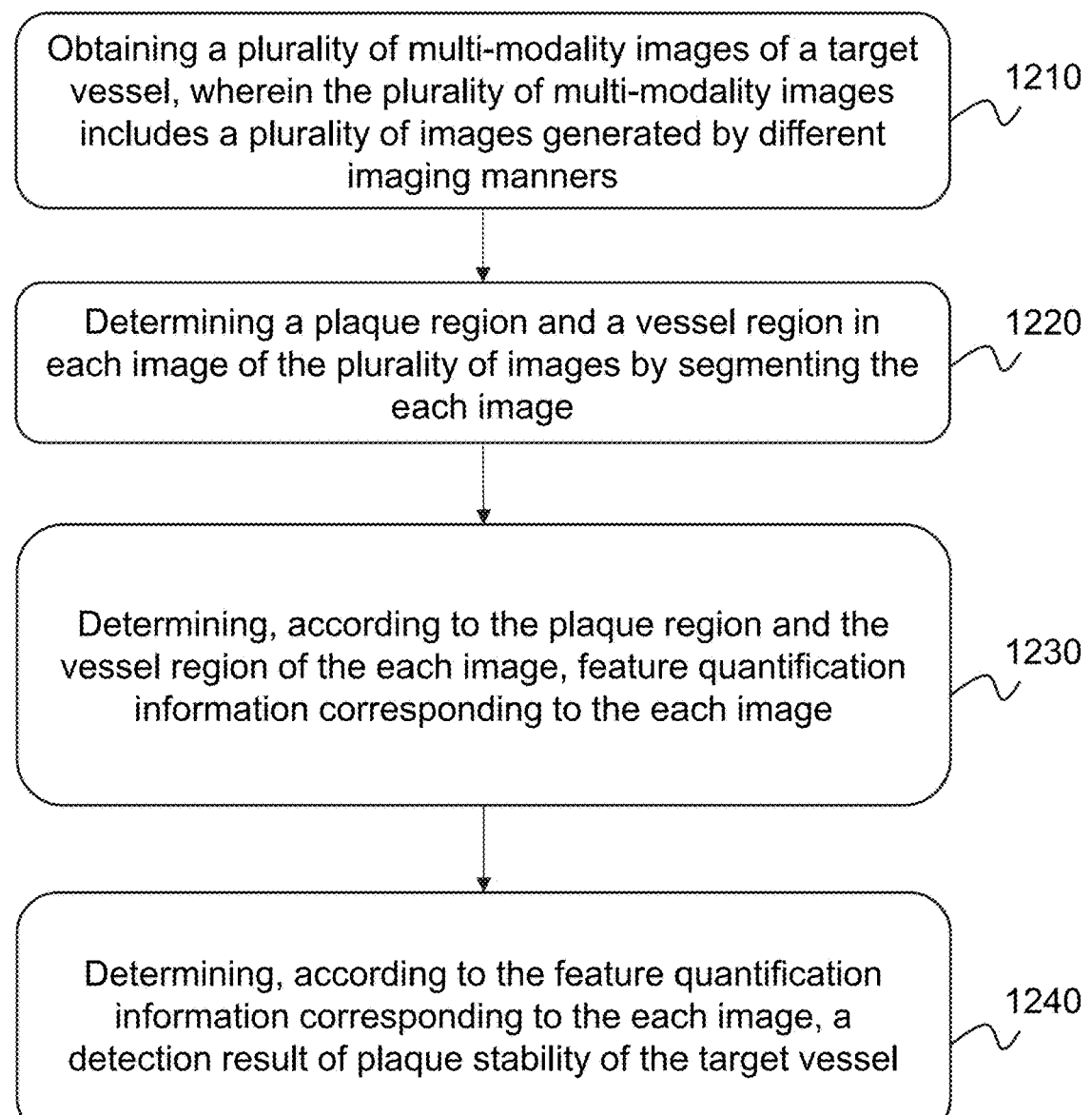
FIG. 12 is a flowchart illustrating an exemplary process for detecting plaque stability according to some embodiments of the present disclosure.

FIG. 12 is a flowchart illustrating an exemplary process for detecting plaque stability according to some embodiments of the present disclosure. In some embodiments, the process 1200 for detecting plaque stability may be performed by the processing device 140 and the stability detection module 240. For example, the process 1200 may be stored in a storage device (e.g., the storage device 150) in a form of a program or an instruction. When the processing device 140 and the medical device 110 executes the program or the instruction, the process 1200 may be implemented. In some embodiments, the process 1200 may be performed by the computing device 300 shown in FIG. 3. As shown in FIG. 12, the process 1200 may include one or more of the following operations.

In 1210, a plaque region and a vessel region in each image of the plurality of images may be determined by segmenting the each image through a trained segmentation model.

In some embodiments, a plurality of images may include a plurality of multi-modality images of a target vessel. The plurality of multi-modality images may be generated by different imaging manners.

In some embodiments, the plurality of multi-modality images may be or include a plurality of sequences of images of a plurality of target vessels. For any target image of the plurality of sequences of images of the target vessel, the computing device 300 may determine N vessel cross-sectional images on N slices according to the vessel centerline and the target vessel plaque of the target image. N may be an integer greater than 0. The plurality of multi-modality image of the target vessel may be 2D images or 3D images.

The computing device 300 may obtain the plurality of multi-modality images of a target vessel, that is, the computing device may obtain a plurality of vessel medical images of a same target object. The plurality of multi-modality images of the target vessel may be the plurality of vessel medical images obtained by scanning the target object with different medical imaging devices, or may also be a plurality of types of vessel medical images obtained by scanning the target object with a same medical imaging device. Different medical imaging devices may include, but are not limited to, a Digital Subtraction Angiography (DSA) device, an ultrasound scanning device, a magnetic resonance device, a computed tomography (CT) device, etc. Various types of data may be obtained using each of the devices. For example, the magnetic resonance device may obtain data such as time of flight (TOF) magnetic resonance angiography, contrast-enhanced magnetic resonance angiography (CEMRA), T1 sequence, T2 sequence, etc. The vessel multi-modality images may be pre-stored in the memory of the computing device. The computing device may directly obtain the vessel multi-modality images of the target object from the memory when required. The types of multi-modality images of the target object and manner(s) for obtaining the vessel multi-modality images of the target object will not be limited in the present disclosure.

In some embodiments, the computing device 300 may determine the plaque region and the vessel region in each vessel medical image by performing feature detection on each vessel medical image in the vessel multi-modality images.

After obtaining the vessel multi-modality images, the computing device 300 may perform feature detection on each vessel medical image included in the vessel multi-modality images, and determine the plaque region and the vessel region in each vessel medical image. The plaque region and the vessel region herein may be independent regions which are segmented from the vessel medical image. The plaque region and the vessel region in vessel medical image may differ in a feature such as a shape, a size, a composition, etc. Therefore, the plaque region and the vessel region in the vessel medical image may be determined and segmented by performing feature detection on the vessel medical image. A manner for performing feature detection on the vessel vessel medical image will not be limited in the present disclosure.

In some embodiments, the segmentation model may further include a fifth segmentation model the computing device 300 may determine the plaque region in the each image by inputting the each image into a trained fifth segmentation model, and extract the vessel region in the each image.

After obtaining each vessel medical image, the computing device 300 may obtain the plaque region in the each vessel medical image, (that is, obtain a position of the plaque region in the vessel medical image) by respectively inputting the each vessel medical image into the fifth segmentation model.

After the computing device 300 determines the plaque region in the each vessel medical image, since the plaque is formed on the vessel, the vessel region in the vessel medical image may be determined according to the plaque region. In other words, the computing device 300 may segment the plaque region and the vessel region in the vessel medical image according to the determined position of the plaque region in the vessel medical image and the vessel medical image, and obtain the segmented plaque region and the segmented vessel region. The computing device 300 may extract the vessel region of the each image based on various algorithms. For example, one or more images may be processed by the trained neural network for extracting vessel regions to extract vessel regions of each image. The extraction manner of the vessel region in the image will not be limited in the present disclosure.

In some embodiments, the fifth segmentation model may be obtained by training a fully convolutional neural network model using a plurality of sample images and a plurality of plaque region labels corresponding to the plurality of sample images. The fifth segmentation model may be obtained by training a fully convolutional neural network model by a computing device using a plurality of medical image samples pre-stored in a memory. The description of the medical image sample may be found in the detailed description of the vessel medical image. The medical image sample may be different from the vessel medical image in that the medical image sample includes a plaque region mark. In other words, the computing device 300 may train the fully convolutional neural network model using supervised training, which can improve accuracy and robustness of determining the plaque region. The fifth segmentation model may be trained by the computing device and stored in the memory, or may be obtained by training the fully convolutional neural network model according to the plurality of medical image samples stored in the memory when needed, which will not be limited in the present disclosure.

In some embodiments, the computing device 300 may determine the plaque region of the each image by inputting the each image into the trained segmentation model (e.g., the fifth segmentation model), and determine the vessel region according to the plaque region and the each image.

In some embodiments of the present disclosure, the plaque region corresponding to the each image may be determined using the trained segmentation model, which can improved efficiency of determining the plaque region and the vessel region in the plaque vessel medical image, thereby improving efficiency of the plaque stability detection method. In addition, the fully convolutional neural network is relatively simple and easy to train.

In some embodiments, an image to be processed corresponding to the each image may be determined according to the plaque region and the each image. The image to be processed may include at least one part of the plaque region and at least one part of the vessel region. The computing device 300 may determine a segmented plaque region and a segmented vessel region by inputting the image to be processed into a segmentation model.

The image to be processed may include the plaque region and the vessel region. The image to be processed may be at least one part selected from each image, which may be a 2D image or a 3D stereoscopic image.

After obtaining the plaque region, the computing device 300 may obtain the image to be processed by segmenting and processing the region where the plaque region is located in the vessel medical image. The image to be processed may include the determined plaque region, as well as the vessel region. In other words, vessel images of most regions may be included in vessel medical images. After determining the plaque region, the computing device 300 may designate the plaque region in the vessel medical image and the vessel region attached to the plaque region as the image to be processed after cropping. The specific manner for determining the image to be processed will not be limited in the present disclosure.

In some embodiments, the segmentation model may further include a sixth segmentation model configured to determine the segmented plaque region and the segmented vessel region. The computing device 300 may determine the segmented plaque region and the segmented vessel region by inputting the image to be processed into the sixth segmentation model and processing the image to be processed by the sixth segmentation model.

In some embodiments, the segmentation model (e.g., the sixth segmentation model) may be obtained by training a convolutional neural network model using a plurality of sample images to be processed, a plurality of sample plaque labels corresponding to the plurality of sample images to be processed, a plurality of sample vessel labels corresponding to the plurality of sample images to be processed. It should be noted that the sample image to be processed may include segmentation mark(s) of the plaque region and segmentation mark(s) of the vessel region, which may be designated as the plurality of sample plaque labels and the plurality of sample vessel labels, respectively.

After obtaining the image to be processed, the computing device 300 may determine the plaque region and the vessel region segmented from the image to be processed by inputting the image to be processed into the trained segmentation model. The description of the sample image to be processed may be found in the detailed description of the above image to be processed, which will not be repeated herein. The sample image to be processed may be different from the image to be processed in that the sample image to be processed includes segmentation mark(s) of the plaque region and segmentation mark(s) of the vessel region. In other words, the computing device may train the convolutional neural network model using supervised training. The segmentation model may be trained by the computing device and stored in the memory, or may also be obtained by training the convolutional neural network model according to the plurality of sample images to be processed stored in the memory when needed, which will not be limited in the present disclosure.

In some embodiments, the segmented plaque region and the segmented vessel region may be determined directly using the trained segmentation model, which can improve efficiency of determining the segmented plaque region and the segmented vessel region, thereby improving efficiency of the plaque stability detection method. In addition, the plaque region in the vessel medical image and the vessel region attached to the plaque region may also be designated as the image to be processed after being cropped, which can avoid analyzing a large count of vessel regions in the vessel medical image, thereby improving efficiency of the plaque stability detection method.

In some embodiments, for the centerline point of interest, the computing device 300 may obtain a target image by determining, from the each image, a cross-sectional image including the centerline point of interest and perpendicular to the vessel centerline.

In some embodiments, the computing device 300 may determine a plurality of reference centerline points on both sides of the centerline point of interest on the vessel centerline, and obtaining a cross-sectional image corresponding to each of the plurality of reference centerline points. For example, n reference centerline points on both sides of the centerline point of interest p on the vessel centerline (i.e., totally 2n+1 reference centerline points including point p) may be respectively determined based on a preset step size ($\lambda$ may be a preset value). Further, 2n+1 cross-sectional images corresponding to the 2n+1 reference centerline points may be obtained. Relevant descriptions may be found in FIG. 5 (the operation 510) or FIG. 7 (the operation 710) and descriptions thereof.

The computing device 300 may obtain an image set according to the target image and the plurality of cross-sectional images corresponding to the plurality of reference centerline points. The image set may include a plurality of image layers. The target image may be one of the plurality of image layers.

In some embodiments, the computing device 300 may obtain a histogram equalized image corresponding to each image layer of the plurality of image layers in the image set by performing histogram equalization processing on the each image layer. Relevant description regarding the histogram equalization processing may be found in FIG. 5 and relevant descriptions thereof.

In some embodiments, the computing device 300 may obtain at least one part of the plaque region by inputting the plurality of image layers and the plurality of histogram equalized images corresponding to the plurality of image layers into a trained segmentation model. Relevant descriptions regarding the segmentation model may be found in FIG. 5 and descriptions thereof.

In some embodiments, the computing device 300 may determine, based on the at least one part of the plaque region corresponding to the each of the at least two centerline points of interest, the plaque region. For example, the computing device 300 may determine the plaque region based on the splicing of the plurality of regions, etc.

In 1220, a detection result of plaque stability of the target vessel may be determined according to the feature quantification information corresponding to the each image.

The feature quantification information may include quantification information of a plurality of plaque features of each vessel medical image and quantification information of a plurality of vessel features of each vessel medical image.

After obtaining the plaque region and the vessel region of each medical image, the computing device 300 may determine the feature quantification information corresponding to the each vessel medical image, that is, the feature quantification information of the plaque regions and the feature quantification information of the vessel regions. The specific manner for the computing device 300 determining the feature quantification information corresponding to the each vessel medical image will not be limited in the present disclosure.

In some embodiments, for the each medical image, the computing device 300 may determine one or more plaque features according to the plaque region, and determine one or more vessel features according to the vessel region. The computing device 300 may obtain the feature quantification information by performing data quantification on the one or more plaque features and the one or more vessel features.

For the each vessel medical image, the computing device 300 may obtain the features of the plaque region, and obtain feature quantification information of the plaque by performing data quantification processing on the features of the plaque region. At the same time, the computing device 300 may obtain the features of the vessel region, and obtain the feature quantification information of the vessel region by performing data quantification processing on the features of the vessel region.

The performing data quantification processing on the features of the plaque region may refer to expressing the features of the plaque region as specific statistics. Similarly, the performing data quantification processing on the features of the vessel region may refer to expressing the features of the vessel region as specific statistics. The quantification information of the plaque features and the quantification information of the vessel features may be collectively referred to as the feature quantification information. The specific features of the plaque region and the specific features of the vessel region is not limited in the present disclosure.

In some embodiments, features of the plaque region and features of the vessel region obtained from the vessel medical images of different modalities may be different. For example, the features of the vessel region that can be obtained from DSA data may be a diameter of a vessel and a degree of stenosis of a vessel, etc. The plaque features that can be obtained from ultrasound data may be a plaque area, a plaque morphology, and a plaque composition, etc. The vessel features that can be obtained from ultrasound data may be parameters of a vessel lumen and a vessel wall of a vessel, a vessel diameter, a stenosis degree of a vessel, and a standardized vessel wall index, etc. The plaque features that can be obtained from CT data may be a basic plaque morphology (e.g., a regularity degree of the plaque, centrality and eccentricity of the plaque), a plaque area, a plaque volume, a plaque composition, a ratio of the plaque area, a ratio of the plaque composition, etc. The vessel features that can be obtained from CT data may be a diameter of a vessel, a degree of stenosis of a vessel, etc. The vessel features that can be obtained from magnetic resonance data may be parameters of a vessel lumen and a vessel wall of a vessel, a stenosis degree of a vessel, etc. The plaque features that can be obtained from magnetic resonance data may be a basic plaque morphology, a plaque area, a plaque volume, a plaque composition, a ratio of the plaque composition, a degree of intensity of the plaque, etc.

In 1230, a detection result of plaque stability of the target vessel may be determined according to the feature quantification information corresponding to the each image.

After obtaining the feature quantification information corresponding to each vessel medical image, the computing device 300 may determine the detection result of the plaque stability of the target object according to the feature quantification information of the plaque region and the feature quantification information of the vessel region in all the vessel medical images. The detection result of the plaque stability of the target object may be configured to characterize whether the plaque of the target object is stable. The specific manner for determining the detection result of plaque stability according to the feature quantification information, and the representation of the detection result of plaque stability of the target object are not limited in the present disclosure.

In some embodiments, if the plaque stability of the target object determined according to the quantification information corresponding to all the vessel medical images is represented by a numerical value, the detection result of the plaque stability of the target object may be expressed in a manner of level classification. That is, when the numerical value of the plaque stability of the target object is within a numerical range to which a level belongs, the detection result of the plaque stability of the target object may be determined to be the level.

In some embodiments, the computing device 300 may determine a vulnerability probability value of the plaque by inputting feature quantification information corresponding to the plurality of images into a probability determination model, and determine the detection result of plaque stability based on the vulnerability probability value.

The computing device 300 may determine the vulnerability probability value of the plaque of the target object by inputting feature quantification information corresponding to all vessel medical images into a probability determination model. The probability determination model may be obtained by training an initial probability determination model using sample feature quantification information and a plurality of vulnerability probability value labels corresponding to the sample feature quantification information.

After obtaining the feature quantification information corresponding to all the vessel medical images, the computing device 300 may obtain the vulnerability probability value of the plaque of the target object by inputting the feature quantification information into a trained probability determination model. The probability determination model may be obtained by training the initial probability determination model using a plurality of sample feature quantification information and a plurality of vulnerability probability value labels corresponding to the sample feature quantification information obtained in advance. The description of the sample feature quantification information may be found in the detailed description of feature quantification information. The vulnerability probability value corresponding to each sample feature quantification information may refer to the vulnerability probability value of the plaque determined under the sample feature quantification information. The initial probability determination model may be a machine learning model or a neural network model. The type of the initial probability determination model is not limited in the present disclosure.

Further, the computing device 300 may determine the detection result of plaque stability based on the vulnerability probability value.

After obtaining the vulnerability probability value of the plaque of the target object, the computing device 300 may determine the detection result of the plaque stability according to the vulnerability probability value. The larger the plaque vulnerability probability value, the easier the plaque is to rupture, that is, the worse the plaque stability. The smaller the plaque vulnerability probability value, the less likely the plaque is to rupture, that is, the better the plaque stability.

In some embodiments, the vulnerability probability value of the plaque of the target object may be determined directly according to the trained probability determination model, so that the detection result of plaque stability may be determined, which can improve the efficiency of determining the detection result of plaque stability. In addition, performing supervised training on the initial probability determination model using the sample feature quantification information, and a plurality of vulnerability probability values corresponding to the sample feature quantification information can improve accuracy and robustness of the method for plaque stability detection.

In some embodiments, the probability determination model may include a regression model or a convolutional neural network model. In other words, the probability determination model may be any one of the regression model and the convolutional neural network model. The regression model may be a linear regression model or a nonlinear regression model.

In some embodiments of the present disclosure, two probability determination models may be proposed, and the user may choose according to an actual application scenario or an actual need, which can improve practicability of the method for plaque stability detection.

In some embodiments, when the probability determination model is a convolutional neural network model, the probability determination model may be obtained by directly training the initial convolutional neural network model according to the sample feature quantification information, and a plurality of vulnerability probability values corresponding to the sample feature quantification information.

In some embodiments, when the probability determination model is a regression model, the sample feature quantification information, and a plurality of vulnerability probability value labels corresponding to the sample feature quantification information may be obtained, and one or more coefficients in the regression model may be determined according to the sample feature quantification information, and the plurality of vulnerability probability value labels corresponding to the sample feature quantification information, thereby obtaining the regression model.

In some embodiments, the computing device 300 may obtain the sample feature quantification information, and a plurality of vulnerability probability value labels corresponding to the sample feature quantification information. The sample feature quantification information may include plaque feature quantification information and vessel feature quantification information. The vulnerable probability value corresponding to the sample feature quantification information may refer to a vulnerability probability value of the plaque determined according to the plaque feature quantification information and the vessel feature quantification information in the sample feature quantification information. The computing device may directly obtain the sample feature quantification information, and the vulnerability probability values corresponding to the sample feature quantification information pre-stored in the memory of the computing device when needed.

The computing device 300 may obtain the regression model by determining, according to the sample feature quantification information and the plurality of vulnerability probability values corresponding to the sample feature quantification information, one or more coefficients in the regression model.

In some embodiments, the regression model may be a linear regression model. The manner for calculating the coefficients of the regression model may be as follows. It is assumed that the sample feature quantification information obtained by the computing device is FN, where N denotes a count of feature quantification information. The mapping function MN corresponding to the sample feature quantification information may be expressed as: $MN=M(FN)$. The linear regression model P may be expressed as: $P=w0+\theta1*M1+\theta2*M2+\ldots+\theta N*MN$, where $\theta$ denotes the regression coefficient of the linear regression model, and w0 denotes the bias term. The regression coefficients in the linear regression model may be calculated through the sample feature quantification information, so that the linear regression model may be obtained.

In some embodiments of the present disclosure, the detection result of the plaque stability of the target object may be determined using the obtained vessel multi-modality images of the target object, that is, the feature quantification information corresponding to the plurality of vessel images, which can improve accuracy of the plaque stability detection of the target object in the case that the plaque stability detection of the target object relies on a lot of data information. In addition, the method for plaque stability detection may be realized by the computing device, and may not need to rely on a doctor, which can improve the detection efficiency, reduce the waste of manpower and material resources, and will not cause inaccurate detection due to the subjective error of the doctor.

It can be understood that, although the operations in the flowcharts are displayed in sequence according to the arrows, these operations are not necessarily executed sequentially in the order indicated by the arrows. The operations are not strictly executed in the order unless explicitly stated herein. The operations may be executed in other orders. Moreover, at least a part of the operations in the flowcharts may include a plurality of operations or a plurality of stages. The plurality of operations or stages are not necessarily performed at a same time, but may be performed at different times. These operations or stages are also not performed necessarily in order, but may be performed alternately or alternatively with other operations or at least a part of the operations or stages in the other operations.

The beneficial effects of embodiments of the present disclosure may include but are not limited to: (1) through multi-slice sections reconstruction, multi-slice vessel cross-sectional images may be reconstructed along the vessel direction at the position of the centerline point, and the 3D information may be introduced while the lightness of the 2D segmentation network is maintained, which can improve the network field of view and the robustness of the segmentation result, thereby improving the accuracy of plaque identification. In addition, the processing of histogram equalization can improve the contrast of the plaque, thereby improving the segmentation accuracy. (2) Based on intelligent and automated plaque composition analysis and stability detection, the efficiency of analysis and detection can be improved, the cost of manpower and material resources can be reduced, and at the same time, the results of analysis and detection can be more accurate. It should be noted that different embodiments may have different beneficial effects. In different embodiments, the possible beneficial effects may include any combination of one or more of the above, or any other possible beneficial effects that may be obtained.

Having thus described the basic concepts, it may be rather apparent to those skilled in the art after reading this detailed disclosure that the foregoing detailed disclosure is intended to be presented by way of example only and is not limiting. Although not explicitly stated here, those skilled in the art may make various modifications, improvements and amendments to the present disclosure. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various parts of this specification are not necessarily all referring to the same embodiment. In addition, some features, structures, or features in the present disclosure of one or more embodiments may be appropriately combined.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. However, this disclosure does not mean that the present disclosure object requires more features than the features mentioned in the claims. Rather, claimed subject matter may lie in less than all features of a single foregoing disclosed embodiment.

In some embodiments, the numbers expressing quantities or properties used to describe and claim certain embodiments of the present disclosure are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the present disclosure disclosed herein are illustrative of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A method implemented on at least one machine each of which has at least one processor and at least one storage device for identifying a plaque, comprising:

obtaining an image set corresponding to a target image, the image set including a plurality of images, the target image being one of the plurality of images;

obtaining a histogram equalized image corresponding to each image of the plurality of images in the image set by performing histogram equalization processing on the each image; and obtaining a plaque identification result of the target image by inputting the plurality of images and/or the plurality of histogram equalized images corresponding to the plurality of images into a trained segmentation model, wherein the trained segmentation model includes a first plaque segmentation model, and the obtaining a plaque identification result of the target image by inputting the plurality of images and/or the plurality of histogram equalized images corresponding to the plurality of images into a trained segmentation model includes:

obtaining a vessel wall mask image corresponding to the target image; and obtaining a first plaque identification result of the target image by inputting the vessel wall mask image, the plurality of images, and the plurality of histogram equalized images corresponding to the plurality of images into the first plaque segmentation model.

2. The method of claim 1, wherein the obtaining an image set corresponding to a target image includes:

obtaining a vessel centerline in an initial three-dimensional (3D) image;

obtaining a centerline point of interest on the vessel centerline;

designating, from the initial 3D image, a cross-sectional image including the centerline point of interest and perpendicular to the vessel centerline as the target image;

taking the centerline point of interest as a starting point, determining a plurality of reference centerline points on both sides of the centerline point of interest on the vessel centerline, and obtaining a cross-sectional image corresponding to each of the reference centerline points; and designating the target image and the plurality of cross-sectional images corresponding to the plurality of reference centerline points as the plurality of images of the image set corresponding to the target image.

3. The method of claim 1, wherein the obtaining a first plaque identification result of the target image by inputting the vessel wall mask image, the plurality of images, and the plurality of histogram equalized images corresponding to the plurality of images into the first plaque segmentation model includes:

performing image normalization processing on the plurality of images and the plurality of histogram equalized images corresponding to the plurality of images;

obtaining first multi-channel input data by merging the vessel wall mask image, the plurality of normalized images, and the plurality of normalized histogram equalized images corresponding to the plurality of images; and obtaining the first plaque identification result of the target image by inputting the first multi-channel input data into the first plaque segmentation model.

4. The method of claim 1, wherein the trained segmentation model further includes a plaque identification model and a second plaque segmentation model, and the obtaining a plaque identification result of the target image by inputting the plurality of images and/or the plurality of histogram equalized images corresponding to the plurality of images into a trained segmentation model further includes:

performing image normalization processing on the plurality of images;

obtaining second multi-channel input data by merging the vessel wall mask image and the plurality of normalized images;

obtaining a plaque type of a plaque in the target image by inputting the second multi-channel input data into the plaque identification model; and in response to a determination that the plaque type is a preset type, obtaining a second plaque identification result of the target image by inputting the second multi-channel input data into the second plaque segmentation model.

5. The method of claim 4, wherein the obtaining a plaque identification result of the target image by inputting the plurality of images and the plurality of histogram equalized images corresponding to the plurality of images into a trained segmentation model further includes:

obtaining the plaque identification result of the target image according to the first plaque identification result and the second plaque identification result.

6. The method of claim 1, wherein the plurality of images include a plurality of sequences of images, the plurality of sequences of images include image information in a same three-dimensional (3D) space, the 3D space includes a plurality of slices, and the method further comprises:

determining a slice of interest in the plurality of slices in the 3D space;

for each sequence of images in the plurality of sequences of images, generating, based on the slice of interest, a vessel centerline of a vessel in the 3D space, and a target plaque of the vessel, a plurality of target slice images corresponding to a plurality of target slices where the target plaque is located, wherein the plurality of target slices include the slice of interest, and the plurality of target slice images include a slice image corresponding to the slice of interest;

determining, according to at least part of the plurality of target slice images corresponding to the plurality of sequences of images, a composition probability map of at least one composition of a plaque on each slice of the plurality of target slices; and determining, according to the plurality of sequences of images, and the composition probability map of the at least one composition corresponding to the each slice, a composition distribution image of the at least one composition of a plaque on the slice of interest.

7. The method of claim 6, wherein the obtaining an image set includes:

for each of at least two centerline points of interest on the vessel centerline, performing operations including:

for the centerline point of interest, obtaining the target image by determining, from at least one sequence of images in the plurality of sequences of images, a cross-sectional image including the centerline point of interest and perpendicular to the vessel centerline;

determining a plurality of reference centerline points on both sides of the centerline point of interest on the vessel centerline, and obtaining a cross-sectional image corresponding to each of the plurality of reference centerline points; and obtaining the image set corresponding to the target image according to the target image and the plurality of cross-sectional images corresponding to the plurality of reference centerline points; and the obtaining a plaque identification result of the target image by inputting the plurality of images and the plurality of histogram equalized images corresponding to the plurality of images into a trained segmentation model includes:

obtaining at least one part of the target plaque by inputting the image set and the plurality of histogram equalized images corresponding to the image set into a first trained segmentation model; and determining, based on the at least one part of the target plaque corresponding to the each of the at least two centerline points of interest, the target plaque.

8. The method of claim 6, wherein the determining, according to at least part of the plurality of target slice images corresponding to the plurality of sequences of images, a composition probability map of at least one composition of a plaque on each slice of the plurality of target slices includes:

obtaining a prior distribution of the at least one composition;

determining an intensity relative map corresponding to each of the at least part of the plurality of target slice images; and determining, based on the prior distribution, the plurality of intensity relative maps corresponding to the at least part of the target slice images, and a preset probability function, a composition probability map of the at least one composition of the plaque on the each slice of the plurality of target slices.

9. The method of claim 8, wherein the determining an intensity relative map corresponding to each of the at least part of the plurality of target slice images includes:

extracting, based on at least one sequence of images in the plurality of sequences of images, a region of interest; and for each of the plurality of target slice images, performing operations including:

extracting, from the each of the plurality of target slice images, a plurality of pixels in the region of interest;

determining a statistical value of the plurality of pixels; and determining, based on the each of the plurality of target slice images and the statistical value, the intensity relative map corresponding to the each of the at least part of the plurality of target slice images.

10. The method of claim 8, wherein the obtaining a histogram equalized image corresponding to each image of the plurality of images in the image set by performing histogram equalization processing on the each image includes:

obtaining the histogram equalized image corresponding to the each of the at least part of the plurality of target slice images by performing histogram equalization processing on the each of the at least part of the plurality of target slice images.

11. The method of claim 8, further includes:

obtaining a segmentation result of a vessel lumen and a vessel wall of the vessel by inputting one or more target slice images corresponding to the at least one sequence of images in the plurality of sequences of images into a second segmentation model;

determining, based on the segmentation result of the vessel lumen and the vessel wall, a contour of the vessel lumen and a contour of the vessel wall;

determining a first distance and a second distance from each pixel in the vessel wall of the vessel to the contour of the vessel lumen and the contour of the vessel wall, respectively; and determining, based on a distance field mapping function, a plurality of first distances and a plurality of second distances corresponding to a plurality of pixels in the vessel wall of the vessel, the distance field map of the vessel.

12. The method of claim 6, wherein the determining the composition distribution image of the at least one composition of the plaque on the slice of interest includes:

obtaining the composition distribution image of the at least one composition of the plaque on the slice of interest by inputting the plurality of sequences of images, the composition probability map of the at least one composition corresponding to the each slice, the intensity relative map corresponding to the each of the at least part of the plurality of target slice images, the histogram equalized image corresponding to the each of the at least part of the plurality of target slice images, and the distance field map into a third segmentation model; and obtaining a composition analysis result of at least one part of the target plaque of the vessel by performing a statical analysis on the composition distribution image of the at least one composition of the plaque on the slice of interest.

13. The method of claim 1, wherein the plurality of images include a plurality of multi-modality images of a target vessel, and the obtaining a plaque identification result of the target image by inputting the plurality of images and the plurality of histogram equalized images corresponding to the plurality of images into a trained segmentation model includes:

determining a plaque region and a vessel region in each image of the plurality of images by segmenting the each image using the trained segmentation model; and wherein the method further includes:

determining, according to the plaque region and the vessel region of the each image, feature quantification information corresponding to the each image; and determining, according to the feature quantification information corresponding to the each image, a detection result of plaque stability of the target vessel.

14. The method of claim 13, wherein the determining, according to the feature quantification information corresponding to the each image, a detection result of plaque stability of the target vessel includes:

determining a vulnerability probability value of the plaque by inputting feature quantification information corresponding to the plurality of images into a probability determination model; and determining the detection result of plaque stability based on the vulnerability probability value.

15. The method of claim 14, wherein the probability determination model includes a regression model or a convolutional neural network model, and the regression model is obtained by:

obtaining sample feature quantification information, and a plurality of vulnerability probability value labels corresponding to the sample feature quantification information; and obtaining the regression model by determining, according to the sample feature quantification information and the plurality of vulnerability probability value labels corresponding to the sample feature quantification information, one or more coefficients in the regression model.

16. The method of claim 13, wherein the determining, according to the plaque region and the vessel region of the each image, feature quantification information corresponding to the each image includes:

for the each image, determining one or more plaque features according to the plaque region, and determining one or more vessel features according to the vessel region; and obtaining the feature quantification information by performing data quantification on the one or more plaque features and the one or more vessel features.

17. A plaque identification system, comprising:

at least one processor; and executable instructions, wherein when executed by the at least one processor, the executable instructions direct the at least one processor to implement a method including:

obtaining an image set corresponding to a target image, the image set including a plurality of images, the target image being one of the plurality of images;

obtaining a histogram equalized image corresponding to each image of the plurality of images in the image set by performing histogram equalization processing on the each image; and obtaining a plaque identification result of the target image by inputting the plurality of images and/or the plurality of histogram equalized images corresponding to the plurality of images into a trained segmentation model, wherein the trained segmentation model includes a first plaque segmentation model, and the obtaining a plaque identification result of the target image by inputting the plurality of images and/or the plurality of histogram equalized images corresponding to the plurality of images into a trained segmentation model includes:

obtaining a vessel wall mask image corresponding to the target image; and obtaining a first plaque identification result of the target image by inputting the vessel wall mask image, the plurality of images, and the plurality of histogram equalized images corresponding to the plurality of images into the first plaque segmentation model.

18. A non-transitory computer-readable storage medium storing computer instructions, wherein when executed by at least one processor, the executable instructions direct the at least one processor to implement a method including:

obtaining an image set corresponding to a target image, the image set including a plurality of images, the target image being one of the plurality of images;

obtaining a histogram equalized image corresponding to each image of the plurality of images in the image set by performing histogram equalization processing on the each image; and obtaining a plaque identification result of the target image by inputting the plurality of images and/or the plurality of histogram equalized images corresponding to the plurality of images into a trained segmentation model, wherein the trained segmentation model includes a first plaque segmentation model, and the obtaining a plaque identification result of the target image by inputting the plurality of images and/or the plurality of histogram equalized images corresponding to the plurality of images into a trained segmentation model includes:

obtaining a vessel wall mask image corresponding to the target image; and obtaining a first plaque identification result of the target image by inputting the vessel wall mask image, the plurality of images, and the plurality of histogram equalized images corresponding to the plurality of images into the first plaque segmentation model.

19. The method of claim 5, wherein the obtaining the plaque identification result of the target image according to the first plaque identification result and the second plaque identification result includes:

obtaining the plaque identification result of the target image by taking a union set of the first plaque identification result and the second plaque identification result.

20. The method of claim 5, wherein the first plaque identification result includes a first plaque identification probability map, the second plaque identification result includes a second plaque identification probability map, and the obtaining the plaque identification result of the target image according to the first plaque identification result and the second plaque identification result includes:

determining an average value, a maximum value, or a minimum value of pixel values of each two pixels at a same position in the first plaque identification probability map and the second plaque identification probability map to obtain a plurality of average values, maximum values, or minimum values; and determining the plaque identification result of the target image according to the plurality of average values, maximum values, or minimum values.

* * * * *